(12) United States Patent
Waters et al.

(10) Patent No.: US 6,391,096 B1
(45) Date of Patent: May 21, 2002

(54) APPARATUS AND METHOD FOR EXTRACTING AND ANALYZING GAS

(75) Inventors: Thomas Waters, Bend; Raymond Bushnell, Milwaukle, both of OR (US)

(73) Assignee: Serveron Corporation, Hillsboro, OR (US)

( * ) Notice: Subject to any disclaimer, the term of this patent is extended or adjusted under 35 U.S.C. 154(b) by 67 days.

(21) Appl. No.: 09/590,510

(22) Filed: Jun. 9, 2000

(51) Int. Cl.$^7$ ............................................. G01N 35/00
(52) U.S. Cl. ................... 96/6; 96/413; 96/417; 73/19.02; 73/23.42
(58) Field of Search ................. 96/6, 8, 10, 157, 96/219, 413, 417, FOR 166; 95/46, 82, 86; 73/19.02, 23.35, 23.36, 23.41, 23.42

(56) References Cited

U.S. PATENT DOCUMENTS

| | | |
|---|---|---|
| 2,180,051 A | 11/1939 | Hickman |
| 3,591,946 A | 7/1971 | Loe |
| 3,631,654 A | 1/1972 | Riely et al. |
| 3,675,395 A | 7/1972 | Baranowski |
| 3,844,160 A | 10/1974 | Yamaoka |
| 3,866,460 A | 2/1975 | Pearce, Jr. |
| 3,894,171 A | 7/1975 | Kusay |
| 3,929,003 A | 12/1975 | Llewellyn |
| 3,992,155 A | 11/1976 | Nilsson |
| 3,998,738 A | 12/1976 | Kusay |
| 4,022,592 A | 5/1977 | Saaski |
| 4,058,373 A | 11/1977 | Kurz et al. |
| 4,070,167 A | 1/1978 | Barbee et al. |
| 4,112,737 A | 9/1978 | Morgan |
| 4,121,352 A | 10/1978 | Lameris |
| 4,236,404 A | 12/1980 | Ketchum et al. |
| 4,374,656 A | 2/1983 | Schrenker et al. |
| 4,385,909 A | 5/1983 | Starr |
| 4,402,211 A | 9/1983 | Sugawara et al. |
| 4,409,814 A | 10/1983 | Onuma et al. |
| 4,437,082 A | 3/1984 | Walsh et al. |
| 4,461,165 A | 7/1984 | Kesson |
| 4,469,495 A | 9/1984 | Hiraizumi et al. |
| 4,498,992 A | 2/1985 | Garrett, Jr. |
| 4,561,866 A | 12/1985 | Altmann et al. |
| 4,604,109 A | 8/1986 | Koslow |
| 4,661,612 A | 4/1987 | George et al. |
| 4,763,514 A | 8/1988 | Naito et al. |
| 4,764,344 A | 8/1988 | Knab |
| 4,834,877 A | 5/1989 | Peters et al. |
| 4,862,729 A | 9/1989 | Toda et al. |
| 4,890,478 A | 1/1990 | Caiborne et al. |
| 4,952,751 A | 8/1990 | Blume et al. |
| 5,104,810 A | 4/1992 | Birbara et al. |
| 5,222,118 A | 6/1993 | Gerth |
| 5,243,848 A | 9/1993 | Cox et al. |
| 5,290,340 A | 3/1994 | Gatten et al. |
| 5,340,384 A | 8/1994 | Sims |
| 5,372,634 A | 12/1994 | Monahan |
| 5,400,641 A | 3/1995 | Slemon et al. |
| 5,423,979 A | 6/1995 | Allen |

(List continued on next page.)

Primary Examiner—C. Scott Bushey
(74) Attorney, Agent, or Firm—Ipsolon LLP

(57) ABSTRACT

A tubular membrane extractor column is connected to an oil filled electrical component such as a transformer. Fault gases dissolved in the transformer oil are extracted from the oil in the separator and are isolated in a second phase. Oil and second phase gas are circulated in separate flow paths until equilibrium is reached. Equilibrated gas is routed to a gas chromatograph or other analytical instrument requiring controlled fluid flow, and which incorporates a manifold assembly that eliminates the need for many of the external fittings and connections required in the instrument. A manifold block has plural fluid flow paths formed therethrough to route fluids to selected components. A collar mates to the block and adapts to a rotary injection valve to provide the continued fluid paths from the block to the injector valve and the other components of the instrument.

5 Claims, 13 Drawing Sheets

U.S. PATENT DOCUMENTS

| | | |
|---|---|---|
| 5,509,294 A | 4/1996 | Gowing |
| 5,509,954 A | 4/1996 | Derian et al. |
| 5,522,917 A | 6/1996 | Honda et al. |
| 5,584,416 A | 12/1996 | Florian |
| 5,659,126 A | 8/1997 | Farber |
| 5,663,492 A | 9/1997 | Alapati et al. |
| 5,686,657 A | 11/1997 | Craig et al. |
| 5,693,122 A | 12/1997 | Berndt |
| 5,749,942 A | 5/1998 | Mattis et al. |
| 5,749,945 A | 5/1998 | Beck |
| 5,753,126 A | 5/1998 | Rohwein |
| 5,762,684 A * | 6/1998 | Hayashi et al. ............... 96/417 |
| 5,830,261 A | 11/1998 | Hamasaki et al. |
| 5,988,703 A | 11/1999 | Craig |

* cited by examiner

APPARATUS AND METHOD FOR EXTRACTING AND ANALYZING GAS

FIELD OF THE INVENTION

The present invention relates to apparatus and methods for removing dissolved gases from liquid and for routing the removed gases to analytical instruments for analysis. More particularly, this invention is embodied in apparatus and method for extracting gases dissolved in electrical insulating oils, and for detecting and analyzing those gases.

BACKGROUND OF THE INVENTION

The electric power industry has for many years recognized that certain electrical and thermal phenomena that occur in oil-insulated electrical apparatus can lead to the generation of a number of "fault gases." These phenomena occur in equipment such as oil filled transformers (both oil-filled and gas-blanketed types), load tap changers, current transformers and bushings and the like. The presence of fault gases may be a measure of the condition of the equipment. As such, detection of the presence of specific fault gases in electrical apparatus, and quantification of those gases can be an important part of a preventative maintenance program.

The presence of fault gases in oil-blanketed transformers and other devices has well documented implications relating to the performance and operating safety of the transformer. There is a substantial body of knowledge available correlating the presence of gases with certain, identified transformer conditions and faults. It is therefore beneficial to monitor the condition of dielectric fluids in electric equipment as a means to maximize performance, and at the same time minimize wear and tear on the equipment, and to thereby minimize maintenance costs and down time. Thus, information relating to the presence or absence of certain fault gases in transformer oil can lead to greatly increased efficiency in the operation of the transformer.

As an example, it is known that the presence of some kinds of fault gases in transformer oil can be indicative of transformer malfunctioning, such as arcing, partial or corona discharge. These conditions can cause mineral transformer oils to decompose generating relatively large quantities of low molecular weight hydrocarbons such as methane, and some higher molecular weight gases such as ethylene and ethane. Such compounds are highly volatile, and in some instances they may accumulate in a transformer under relatively high pressure. This is a recipe for disaster. Left undetected or uncorrected, these volatile gases can lead to an increased rate of degradation, and even to catastrophic explosion of the transformer. Transformer failure is a significantly expensive event for an electric utility, not only in terms of down time and the costs of replacement equipment, but also in terms of the costs associated with lost power transmission. On the other hand, by closely monitoring dissolved gases in transformer oil, the most efficient operating conditions for a given transformer can be actively monitored and the transformer load may be run at or near a maximized peak. Moreover, when dangerous operating conditions are detected the transformer can be taken off line for maintenance.

Despite the known need for reliable equipment to monitor gas in oil, designing equipment has been problematic for a variety of reasons. There have been many attempts to solve the problems associated with transformer gas-in-oil monitoring, but none of them ideal. Some electrical utilities routinely sample transformer oil in the field, extract gas sample aliquots and return the samples to laboratories to run dissolved gas analysis, often with laboratory GCs. Sometimes portable field GCs can be used, as well. But these methods do not give real-time analysis and may result in data that is not a true measure of actual, ongoing operating conditions. Moreover, physical sampling cannot be done on a continuous, ongoing basis, and instead requires scheduled visits. Sample analysis and historical data are thus based on widely intermittent sampling protocols rather than continuous sampling. But an intermittent sampling protocol may entirely miss a substantial transient transformer fault. That is, it is unlikely that the timing of an intermittent sampling will correlate with a specific fault event. Moreover, it is well known that each transformer tends to have a unique set of operating conditions and tends to run under certain conditions unique to that transformer. In essence, each transformer has a set of normal operating conditions that are unique to that unit. Knowledge of a transformer's normal operating conditions allows for accurate prediction and analysis of when a certain out-of-normal condition is a true fault condition or an event that might be expected. With periodic sampling it is all but impossible to develop an accurate operating profile for each transformer.

One practical result of such difficulties in such sampling and other factors has been that, out of safety and maintenance concerns, many commercial power transformers are run at loads that are significantly less than the transformer is capable of handling. Alternately, transformers are run at loads closer to their operating maximum without sufficient information about the existence of possible dangerous conditions, which could lead to catastrophic failure. This protocol for operating transformers is inefficient, expensive and in some cases dangerous.

Mechanical/vacuum and membrane extraction methods and apparatus for degassing transformer oil are also well known in the art. As one example, U.S. Pat. No. 5,659,126 discloses a method of sampling headspace gas in an electrical transformer, analyzing such gases according to a temperature and pressure dependent gas partition function, and based on the derived analysis predicting specific transformer faults. An example of a gas extraction apparatus that relies upon a membrane for extraction of gas from transformer oil is disclosed in U.S. Pat. No. 4,112,737. There, a probe having a plurality of membrane tubes is inserted directly into transformer oil in the transformer housing. The material used for the membrane is impermeable to oil, but gases dissolved in the oil permeate through the membrane into the hollow interior of the tubes. A portable analytical device such as a portable gas chromatograph is temporarily connected to the probe so that the test sample is swept from the probe into the analytical device for analysis.

Although these devices have provided benefits, there are numerous practical problems remaining to the development of reliable apparatus for extraction, monitoring and analysis of fault gases in transformer oils. Many of these problems relate to the design of reliable fluid routing systems that are redundant enough to provide a relatively maintenance free unit. Since transformers are often located in exceedingly harsh environmental conditions, fluid routing problems are magnified. This is especially true given that the instruments needed to reliably analyze the gases are complex analytical instruments.

Many chemical analytical instruments rely upon controlled and accurate fluid flow through the instrument during analytical processing. Such instruments include machines designed to perform chemical analysis of various types, purify samples and to perform monitoring of various aspects of laboratory and commercial processing. To name just a few of the types of analytical instruments in which precise fluid flow is a critical part of the functioning of the machines, there are gas chromatographs (GCs) of numerous types, spectrophotometers of many kinds, and many other similar instruments. Gas chromatographs, for example, rely upon accurate control and processing of known quantities of fluid flowing through separation columns during the analytical processing. Without accurate control of fluid flow, analytical results are compromised.

In a GC the fluid is in the form of gas. Samples of fluid under test are typically under the control of control devices such as pumps, valves, pressure transducers and pressure regulators. The control devices help in the acquisition of samples, and the isolation, handling and separation of the samples during the process of chemical analysis. In a GC, a sample aliquot is directed, either manually or automatically, through a complicated array of plumbing hardware and control systems that that perform various functions before the sample flows through one or more separation columns. In the separation columns different compounds in the sample fluid are isolated. As the isolated compounds flow out of the columns they flow through detectors of various kinds that assist in identifying and quantifying the compounds.

As a sample flows through an instrument such as a GC it may be exposed to various other fluids such as carrier fluids, calibration fluids and the like. Moreover, the fluid flow paths include many junctions and intersections. At each step along the processing path where fluids are rerouted or further isolated, the fluid flows through a variety of plumbing hardware and control systems.

It is obvious that in many analytical instruments that require controlled fluid flow there are numerous fluid flow paths, and complex hardware systems that include tubing, barbs, couplings, valves, sensors, pumps and regulators of various kinds. The plumbing systems in even relatively simple instruments such as some gas chromatographs can become exceedingly complicated, not to mention the complexity added by the fluid control systems.

Precision, reliability and accuracy are of course primary goals of any analytical analysis. As such, it is essential in an analytical instrument to eliminate, or at least minimize, all sources of system failure, including problems such as leaking fittings that can adversely effect the analytical processing. The complexity of the plumbing and fluid controlling hardware of many analytical instruments presents a situation that is at odds with the fundamental principles of accuracy and precision that such instruments rely upon. Accurate analytical results require accurate fluid processing, without system failures such as non-fluid-tight couplings. But every fitting, connection, interconnection and fluid-controlling device in an analytical instrument introduces a potential site for a problem such as a leak. When even a small leak occurs in a critical connection the accuracy of analytical test data is compromised. In an instrument that contains dozens of couplings and connections the opportunity for incorrectly connected fittings is multiplied many times over.

The problems described above with respect to complicated fluid connections are well known to any laboratory technician who has operated an analytical instrument such as those described. Even in the relatively idealized conditions of a modern laboratory, and even with laboratory grade instruments, plumbing problems are a constant source of trouble with analytical instruments such as GCs. As such, there is a great benefit in reducing the number and complexity of fittings in an instrument that uses fluid flow.

But the problems noted above are even more pronounced with analytical instruments that are designed for use in the field rather than in a controlled laboratory environment. There are several reasons. First, field instruments tend to be smaller since portability may be a primary goal. As the instruments get smaller so do the fittings and connections. With miniaturized-hardware it is more difficult to ensure fluid-tight processing. Second, an instrument designed for use in the field is often subject to more extreme environmental conditions and rougher handling. In many respects, therefore, field units need to be even more robust than their laboratory counterparts. This can be a difficult objective when another goal in designing the unit is reduction of size.

A relatively newer type of analytical instrument is an in-situ monitoring device that is installed in place to monitor on an ongoing basis some kind of processing activity. Such devices are often designed to interface with telephony equipment for automatic transmission of analytical data and for remote access to central processing units in the instruments. These devices may be left in the field for extended periods of time, and do not have the benefit of the constant monitoring and maintenance that both laboratory and portable instruments might enjoy. In-situ instruments therefore must be extremely rugged to provide reliable data over an extended period of time.

In-situ instruments also may be placed in extreme environmental conditions that test the limits of hardware design. For instance, such devices may be subjected to wide fluctuations in ambient temperature and other extremes in weather conditions, and to harsh chemical environments. Design engineering must take these conditions into account. But in instruments that include complicated plumbing schemes it is even more difficult than in laboratories to minimize chances for leaking fittings and the accompanying errors in obtaining reliable data.

There have been various attempts made at developing in-situ analytical instruments for continuous monitoring and analysis of dissolved gas in transformer oil. Some of these attempts have shown some promise of success. Others have not fared as well. Regardless, the in-situ analytical instruments are often subjected to extremely harsh environmental conditions. For example, as noted, power transformers may be located in areas where ambient temperatures vary from extreme cold in winter months to extreme heat in summer. Furthermore, all large transformers are prone to vibration during operation that can be significant. Such vibration on a continued basis can be very rough on equipment near the transformer. All things considered, it is very difficult to design an accurate, precise and rugged analytical instrument that can withstand these environmental conditions without repeated failures.

The problems described above with complicated plumbing, control and hardware systems are amplified many times over in the extreme conditions found at transformer locations. The extreme temperature variations can cause thermal expansion and contraction that leads to leaking fittings and other connections, and environmental vibrations can, over time, loosen fittings and damage sensitive connections.

Therefore, despite advances in the technological solutions surrounding analytical instruments designed to sample, analyze and report data from remote locations, there is a need for a fluid handling system that is rugged and redundant enough that it will function without failure and without regular maintenance. Such a fluid handling system would be advantageously and beneficially used in both field instruments and in laboratory grade instruments.

While there are many different approaches to the actual degassing of oil from electric power transmission equipment, any in-situ approach must be designed to ensure fluid-tight processing. This is important for several reasons. First, failure of an oil transfer line can lead to transformer insulating oil escaping from the transformer. Left undetected, loss of oil can lead to transformer failure. Leaking oil is also an environmental concern. Second, an analytical system that introduces gases from the analytical instrument to the transformer creates problems independent of transformer performance, and is unacceptable. These problems are particularly difficult with regard to the fluid connections associated with the degassing apparatus, whether located within the transformer or adjacent to it.

SUMMARY OF THE INVENTION

The advantages of the present invention are achieved in a first preferred embodiment of a gas extraction apparatus that provides for accurate extraction of dissolved gases and for fluid-tight handling of both oil and extracted gas. The apparatus utilizes an extraction module comprising plural composite hollow fiber tubes coated with a thin layer of a non-porous gas permeable polymer, making each tube gas, but not dielectric fluid permeable. The extraction module is contained within a fluid-tight cartridge housing. The apparatus includes and is plumbed to an analytical instrument such as a gas chromatograph that utilizes a ported manifold for routing and controlling fluid flow into and through the instrument. The ported manifold includes isolated fluid flow paths that eliminate plural fittings and hardware plumbing devices. The manifold is mated to a cooperatively ported collar or flange, which is designed to mate with a rotary injector valve. Fluid control apparatus such as pressure transducers, valves and pressure regulators are connected directly to the ported manifold and are fluidly connected with appropriate fluid streams in the manifold. The combination of the manifold and collar and the manner in which the collar mates with the rotary injector valve provides for a rugged and redundant fluid flow system that eliminates the vast majority of fittings normally found in analytical instruments.

BRIEF DESCRIPTION OF THE DRAWINGS

The invention will be better understood and its numerous objects and advantages will be apparent by reference to the following detailed description of the invention when taken in conjunction with the following drawings.

DETAILED DESCRIPTION OF A PREFERRED EMBODIMENT

Figure 1:
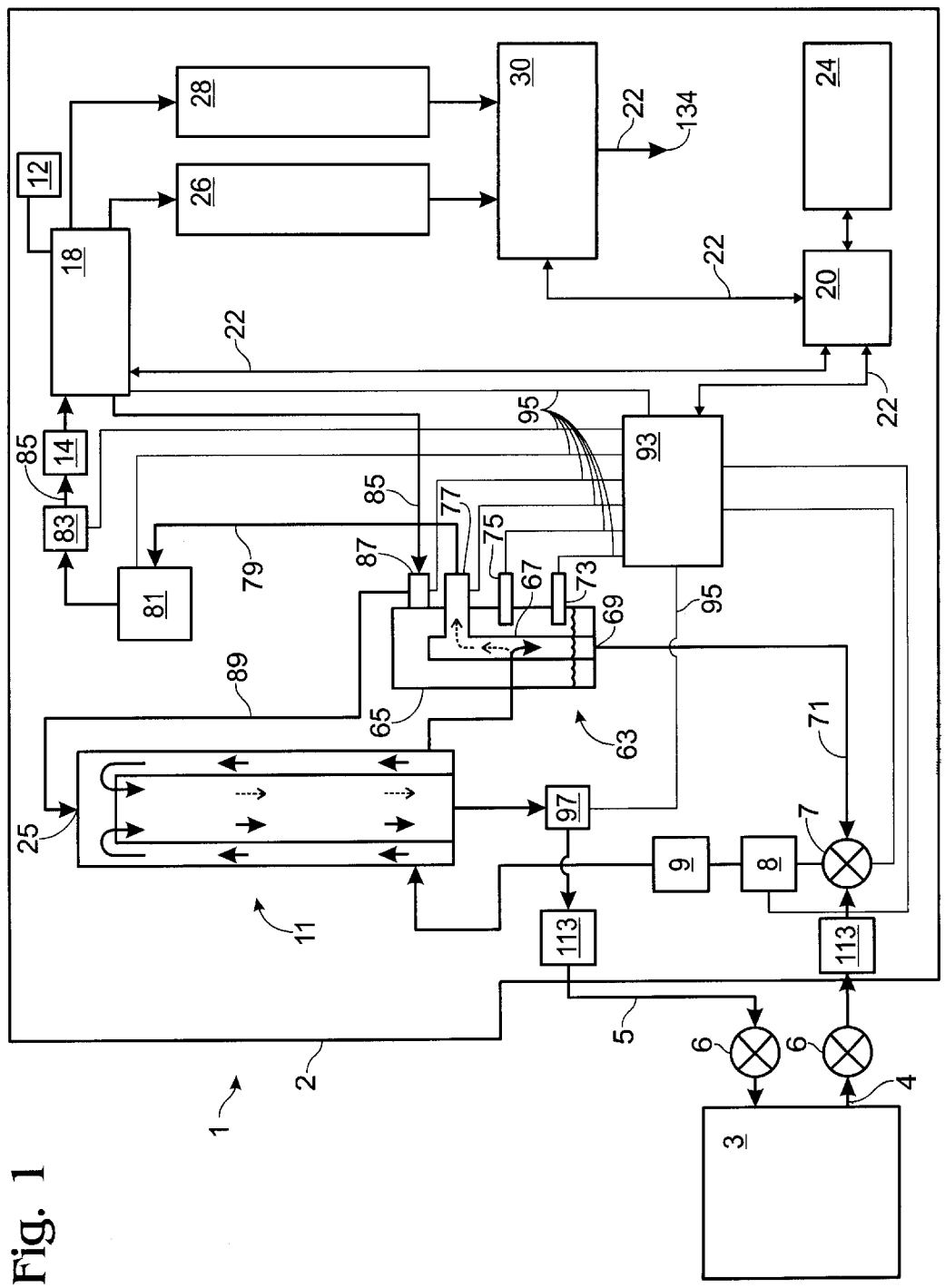
FIG. 1 is a simplified block diagram showing a gas extraction and analyzing apparatus in accordance with the present invention, and fluidly connected to a source of fluid to be analyzed.

The basic components of the gas extraction and analyzing apparatus of the present invention will be described generally first, then a more detailed description of certain components will follow. With reference to FIG. 1 it may be seen that the gas extractor and analyzer 1 of the present invention is contained in a housing 2 that is located externally to the oil-filled or blanketed electrical device 3 that is being monitored. Electrical device 3 is typically an oil-filled or oil-blanketed transformer, load tap changer, etc. A sample fluid supply line 4 is connected to electrical device 3 and delivers sample fluid to the components contained in housing 2. A sample fluid return line 5 likewise returns sample fluid to the electrical device from the analyzer 1. Extractor/analyzer 1 has been designed to be operable over extended periods of time without maintenance. Accordingly, numerous safeguard systems and backup systems have been incorporated. For example, control valves 6, such as check valves, are incorporated into supply line 4 and return line 5. In the event one of the supply lines was damaged, the control valves provide a means for preventing oil from draining from electrical device 3, which could lead to failure of the device.

Following generally the flow of sample fluid within housing 2, fluid is routed first through an inline filter 113 to a control valve 7 that is a three-way control valve that in normally operation is open to direct sample in a fluid line through pump 8 past pressure transducer 9 and into extractor assembly 11. Filter 113 in supply line 4 prevents any contaminants within electrical device 3 from entering analyzer 1. The other inlet to control valve 7 is normally closed. Pump 8 is preferably a controlled, variable speed gear pump. Sample containing fluid (i.e. oil) flows through extractor assembly 11 in a manner detailed below, where gas dissolved in the oil is extracted into a second fluid phase for further processing. The oil is returned to electrical device 3 through fluid return line 5, which incorporates a second inline filter 113 to remove any impurities that may be contained within the sample fluid and to thus avoid any contamination of the fluid in electrical device 3.

Sample line 4 is preferably attached to electrical device 3 at a point of high oil flow to insure that a representative sample of fluid is always flowing through extractor assembly 11. The location of the connection of the fluid return line 5 to electrical device 3 is not critical other than it being separated by a sufficient distance from the fluid supply line to not exchange substantially the same fluid. Specifically the fluid sample line can be attached to the oil fill valve on a transformer, a drain valve on an oil radiator, or an oil by-pass loop, for example. The fluid return line, on the other hand, may be attached to the bottom drain valve to return the oil to the transformer, or other suitable positions. Typically, there is no need to tap special ports into the transformer since the oil supply and return lines may be ported into existing locations.

As described below, the present invention relies upon principles of diffusion across a membrane to extract gases from a first fluid phase where gas is in a relatively higher concentration, into a second fluid phase where the gas is in a relatively lower concentration. Typically, the first fluid phase is the transformer insulating oil and the second fluid phase is the gas contained within the gas analysis components of the system.

Figure 2:
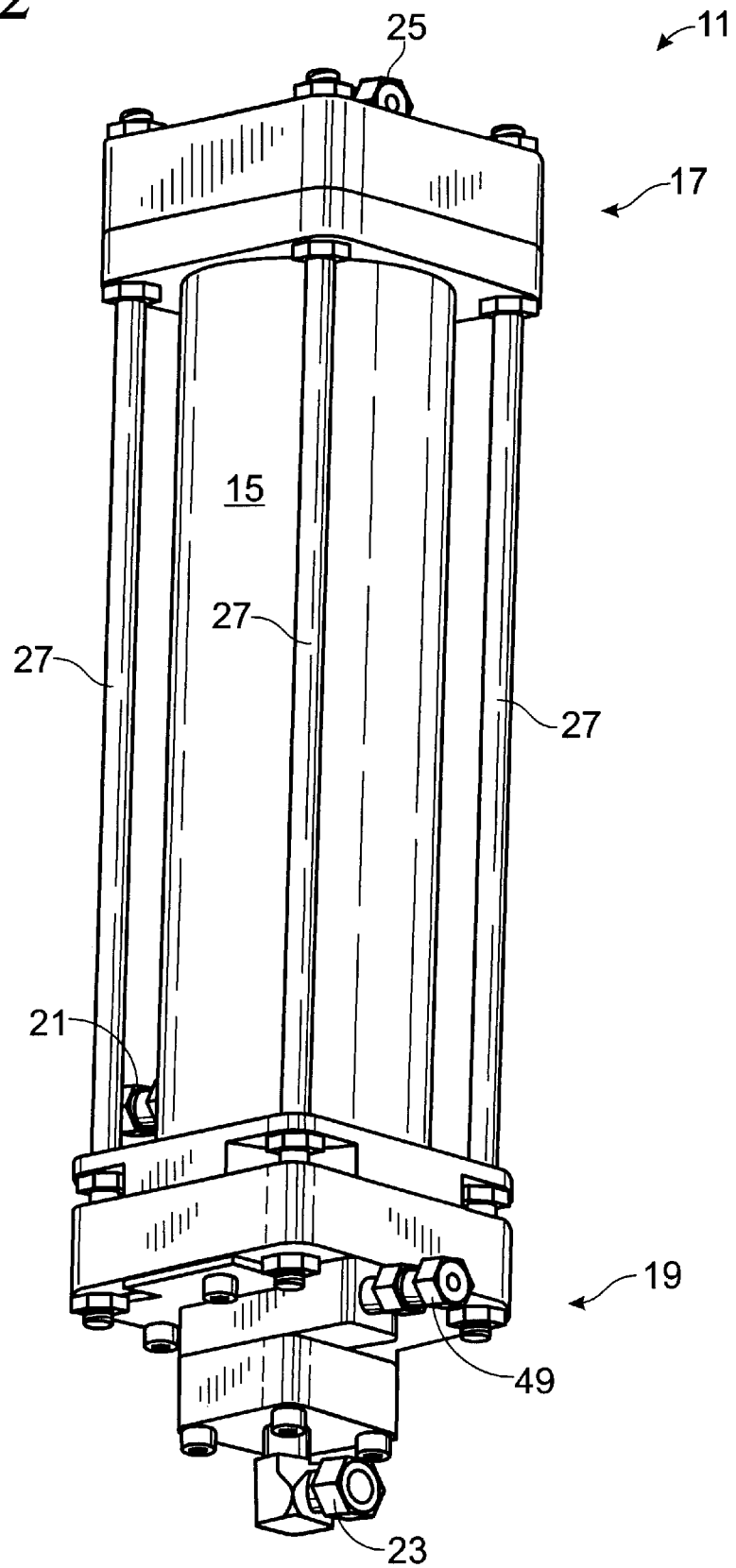
FIG. 2 is a perspective view of an extractor assembly according to the present invention.
Figure 3:
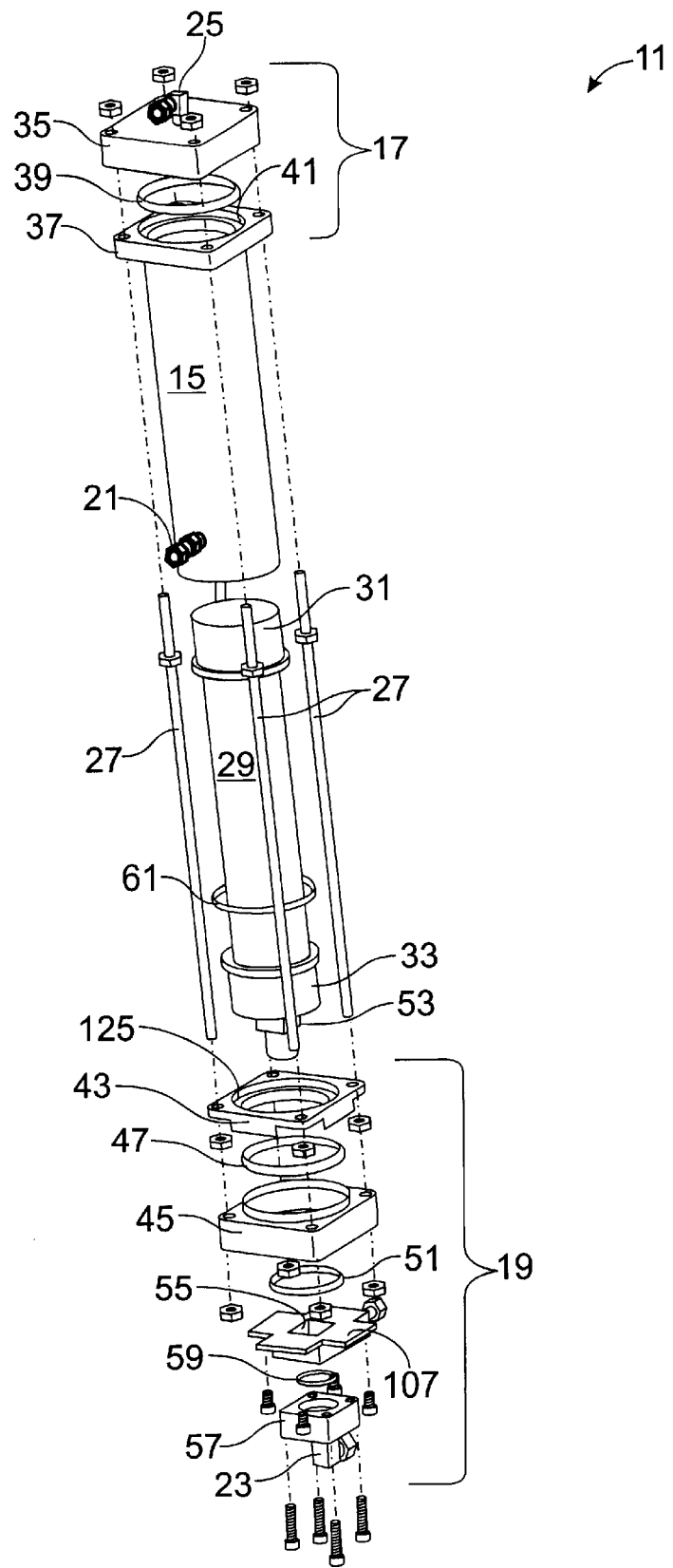
FIG. 3 is a perspective exploded view of the extractor assembly shown in FIG. 2.

The construction of extractor assembly 11 is shown in detail in FIGS. 2 and 3. Referring to FIG. 2 assembly 11 includes a tubular filter cartridge housing 15 bounded on opposite ends by a top seal assembly 17 and a bottom seal assembly 19. A fluid inlet 21 is in located near the lower end of cartridge housing 15 and a fluid outlet 23 is at the lower end of the bottom seal assembly. A gas inlet 25 is located at the upper end of top seal assembly 17. A gas outlet 49 is located on the lateral side of bottom seal assembly 19. Extractor assembly 11 is hermetically sealed and is designed to provide fluid-tight connections in all respects. Most parts of the assembly are preferably stainless steel, although other materials may be used. Inlets 21 and 25 and outlets 23 and 49 are welded to the respective seal assemblies to ensure fluid tight connections. A system of O-ring seals is included and is detailed below. Threaded rods 27 extend around the periphery of the assembly and are torqued to hermetically seal the assembly.

In use, assembly 11 is oriented such that the longitudinal axis of housing 15 is positioned vertically. Hence the naming convention utilizing "top" and "bottom."

Extractor assembly 11 is shown in an exploded view in FIG. 3. A filter cartridge 29 is contained within cartridge housing 15. Filter cartridge 29 comprises a plurality of tubes (not detailed), each of which comprises a composite hollow fiber coated with a thin layer of a non-porous gas permeable polymer. The number of hollow fibers and their dimensions are variable and dictated by their application, but preferably have inner and outer diameters of approximately 460 um×640 um and are of sufficient number to give a total surface area of approximately 4,000 cm2. The hollow fibers are preferably aligned parallel to the length of cartridge 29 and may be cemented to each other at opposite ends by a bed of cured resin such as polyurethane or epoxy. The ends of the hollow fibers terminate in upper end cap 31, and lower end cap 33, respectively, which allow the second fluid phase (i.e., gas) to flow through the interior of the hollow fibers and the first fluid phase (i.e., oil) to flow around the exterior of the hollow fibers.

A suitable filter cartridge 29 for use with the present invention is available from Compact Membrane Systems, Inc., Wilmington, Del. Hollow fibers suitable for this invention can be fabricated from various porous materials, including polypropylene, polyvinylidene fluoride, but preferably polysulfone. The fibers preferably have pores sufficiently small (0.02–0.03 microns) to give a molecular weight cut off (MWCO) value of about 50,000. The inside and/or outside of the hollow fibers can be coated with a thin non-porous layer varying in thickness from 0.01–10 microns of an amorphous copolymer of perfluoro-2,2-dimethyl-1,3-dioxole (PDD) and varying amounts of tetrafluoroethylene (TFE). Other fluoropolymers may also be successfully used. Two specific copolymers are Teflon® AF 2400 and Teflon® AF 1600 available from E. I. du Pont de Nemours and Co, Wilmington, Del. Such coatings are generally used to improve selectivity towards specific gases during gas separations and for oxygen enrichment from air. In the present application, this layer acts as a barrier to the dielectric fluid but is sufficiently permeable towards small molecules, allowing rapid diffusion of gases, moisture and volatile compounds while retaining the dielectric fluid fraction. The fibers may be coated with any non-porous and gas permeable coating, preferably a fluoropolymers coating.

Although not detailed in the drawings, the filter cartridge 29 includes an oil impermeable sleeve that surrounds all of the tubes and which is connected to the cartridge at the lower end cap (described below) and terminates below upper end cap 31. The sleeve defines an annular space between the exterior of the sleeve and the interior of the cartridge housing. This permits oil to flow into housing 15 through inlet 21, upwardly in the annular space and over the upper edge of the impermeable sleeve. From this point the oil flows downwardly, around the spaces between the plurality of tubes in the filter cartridge 29.

The exterior side of the tubes define a first phase side that is bounded by cartridge housing 15. The interior of the tubes defines a separate, second phase side within the tubes. That is, there is a first phase side for the oil, and a separate second phase side for the gas that is extracted from the oil. Fluid such as oil (shown in the solid arrows in FIG. 1) containing entrained or dissolved contaminants such as gas, moisture and other volatile compounds of interest is introduced into extractor assembly 11 through inlet 21 under the flow control of pump 8. Oil fills the first phase side and coats all of the tubes and flows past the tubes. An atmospheric condition or diffusion gradient is created across the two different phase sides. That is, where contaminants are in relatively higher concentration on the first phase side they diffuse across the phase barrier defined by the tubes to the second phase side (in the interior of the tubes) where there is a relatively lower concentration of the contaminant. This is schematically illustrated by the "dashed-line" arrows and the solid arrows in FIG. 1, the dashed arrows representing the second phase side. The diffusion will continue until equilibrium exists on both sides of the phase barrier. The atmospheric condition may be created in one of several ways, for instance with passive diffusion or active diffusion with, for example, a vacuum applied to the second phase side.

As indicated with the solid and dashed arrows in FIG. 1, contaminants from the first phase side (i.e., the oil phase) diffuse into the second phase side for further processing, which is described below.

Returning to FIG. 3, top seal assembly 17 and bottom seal assembly 19 are designed to ensure a fluid tight, hermetic seal. Top seal assembly 17 comprises a cap plate 35 that cooperatively mates to a base plate 37 that is welded to cartridge housing 15. An O-ring 39, preferably made of Viton™ is fitted in an annular space between cap plate 35 and base plate 37. Specifically, base plate 37 includes an annular, angular shoulder 41 for receiving O-ring 39. A cooperatively formed annular, angular shoulder on cap plate 35 mates to shoulder 41 with the O-ring being crushed therebetween to provide a fluid-tight seal, and to establish an inlet for the second fluid phase from inlet 25 to the interior of the tubes.

Bottom seal assembly similarly provides a hermetically sealed connection. A base plate 43 includes an O-ring groove 125 that receives an O-ring 61. The diameter of groove 125 is the same as the diameter of cartridge housing 15. As such, when the housing is assembled with the base plate the housing forms a fluid-tight seal against O-ring 61. Base plate 43 mates to a crush plate 45 in the same manner described above with an O-ring 47. The bottom seal assembly provides for handling of the two different fluid phases, the oil phase and the separated gas phase. A gas outlet plate 107 having a gas outlet port 49 is mated to crush plate 45 with an O-ring 51 fitted therebetween. The bottom end cap 33 of filter cartridge 29 defines a gas outlet extension 53 that cooperatively mates with an opening 55 in crush plate 45. This defines a separate fluid path for the gas contained in the second phase. Oil flowing through extractor assembly is fluidly routed in a separate fluid path defined in bottom seal assembly 19 through fluid outlet 23, past thermocouple 97 and to the electrical device 3. Thus, bottom plate 57 is sealed to gas outlet plate 107 with an O-ring 59 to define a fluid path for oil. As detailed in FIG. 3, extractor assembly 11 is connected with screws and the like, which are sufficiently tightened to provide the necessary fluid tight connections.

Returning now to FIG. 1 it may be seen that the two phases of fluid separated in extractor assembly 11 are directed into and flow through different and isolated fluid paths. The gas phase comprising gas extracted from the oil phase flows through outlet 49 to a plenum assembly 63. It has been found that even with the most efficient phase barriers known for use with filter cartridge 29, some of the first fluid phase (i.e., the oil) diffuses across the tubes into the second fluid phase (i.e., the gas). This is an undesirable result since the gas phase is, when this occurs, essentially contaminated with the fluid from the first phase, and has been a major source of problems with known separation systems. Since the second fluid phase is a gaseous phase that is to be analyzed in a gas chromatograph, the presence of liquid could present a damaging condition. Any oil diffusing into the gas phase therefore must be removed. This is accomplished in plenum 63.

Plenum assembly 63 comprises a vertically oriented housing 65 containing an internal plenum 67. Gas extracted in extractor assembly 11 is fluidly piped into the lower portion of plenum 67. Any first phase fluid (i.e., oil) that inescapably diffuses into the second fluid phase also flows into the lower portion of plenum 67. Plenum 67 is oriented vertically. The heavier oil flows downwardly (see the arrows in FIG. 1) through an outlet port 69 that is plumbed through tubing 71 to control valve 7. As noted earlier, in normal operation control valve 7 is normally opened toward oil pump 8 and is normally closed to the source of oil from plenum 67. Oil accumulates in tubing 71 and in the lower portion of plenum 67 until the oil level in the plenum is detected by a first sensor 73, which is preferably an optical sensor under the control of a computer 20. When first sensor 73 detects oil in the plenum, control valve 7, which also is under the control of computer 20, is switched such that pump 8 pumps oil out of tubing 71 and plenum 67, routing the fluid back into extractor assembly 11. As noted above, pump 8 is preferably a gear pump. Computer 20 is informed of the volume of fluid that is pumped by pump 8 with each rotation of the gears in the pump. Computer 20 allows pump 8 to run for a period of time corresponding to the desired volumetric pumping sufficient to pump most of the fluid out of tubing 71. When the desired volume has been pumped from tubing 71, valve 7 is again switched. It will be appreciated that even if some of the second fluid phase is pumped back into extractor assembly 11 during this operation, the second fluid will accumulate in the upper end of the assembly, where it will eventually diffuse back into the second phase without interfering with normal operations.

A second sensor 75 is positioned vertically above first sensor 73 and provides a failsafe to prevent oil from reaching the downstream components, which could be damaged by contact with oil. Second sensor 75 is also preferably an optical sensor under the control of computer 20. If it detects oil in the plenum then computer 20 prompts system shut down. Shut down provides a monitoring capability to prevent catastrophic failure, and is also an indicator that the filter cartridge 29 is either leaking or has worn out and should be replaced.

In normal conditions the gaseous second phase flows upwardly in plenum 67 past second sensor 75 through control valve 77 and tubing 79 to gas pump 81. The gas is pumped from pump 81 past a pressure transducer 83 to valves on a manifold assembly 18 (described in detail below). The system is calibrated to allow gas to diffuse through the tubes in filter cartridge 29 over a period of time so that the system approaches equilibrium. This provides a true measure of the concentration of dissolved gas in the oil, which in turn facilitates accurate analysis and diagnosis by the software associated with the gas chromatograph. The time required to reach equilibrium or near equilibrium conditions depends upon factors such as pressure and temperature, the size of the diffusing molecules and the pore size of the media, as well as the flow rate of the oil carrying the gases for equilibrium. While equilibrium is being established, the valves in manifold assembly 18 route the gas through tubing 85 to a control valve 87 on plenum housing 65, then through tubing 89 back to gas inlet 25 on extractor assembly 11.

The fluid control and handling components of the present invention are useful in many kinds of analytical instruments that have a need for controlled and accurate delivery and routing of fluids. One preferred embodiment of the invention is described with reference to a gas chromatograph that is designed for installation in a remote location and is designed for automated operation under the control of a programmed computer. This in-situ device utilizes telephony equipment so that analytical results may be acquired remotely. As used herein in the description of a preferred embodiment the word fluid refers to gases that flow through the instrument. However, the invention may be used with apparatus that use liquids and therefore the word fluid relates to any fluid that might be used in an analytical instrument.

Figure 4:
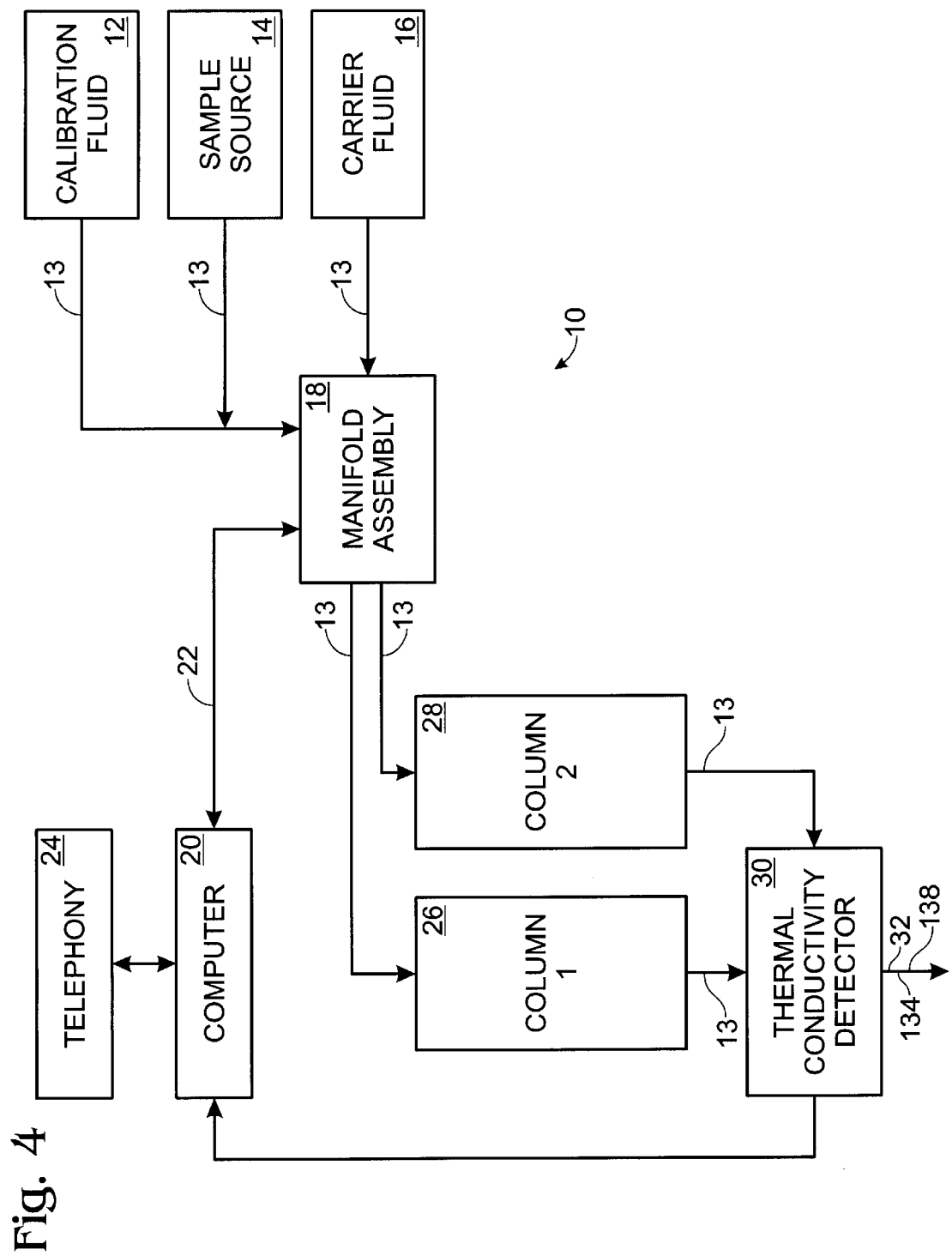
FIG. 4 is a simplified block diagram showing an analytical instrument including the components of the present invention.

With reference to FIG. 4, a gas chromatograph 10 is shown as including a source of calibration gas 12, a sample source 14 for samples that are to be analyzed (i.e., samples extracted in extractor assembly 11), and a carrier fluid 16 which typically is supplied as a high pressure inert gas such as helium. Each of these sources of fluid (in this case the fluid is gaseous) is fluidly connected to a manifold assembly, generally referenced with numeral 18. The fluid connections between the source fluids 12, 14 and 16 are accomplished with appropriate fluid lines 13 such as stainless steel tubing. Fluid lines 13 are fitted with appropriate passive fittings such as sealed, screw-type fittings and the like. All connections between fluid lines 13 and other components, such as components of manifold 18, are fluid-tight connections with appropriate gaskets and O-rings and the like.

As described in detail below, manifold assembly 18 includes several components, including active fluid handling and control components that are under the active control of a computer 20. Computer 20 is connected to and sends command signals to and received data from components associated with manifold assembly 18 by way of data lines 22. The command signals control operation of the chromatograph. Computer 20 is connected to telephony equipment 24 so that computer 20 may be operated from a remote location, which thus allows the chromatograph to be operated remotely and for data from the chromatograph to be acquired from a remote location. Computer 20 also controls an extractor control board 93 (FIG. 1), which in turn includes circuitry and state machines that monitor and control the gas extraction assemblies as illustrated with data lines 95.

The word computer is used generically herein for a programmed device capable of controlling operations of chromatograph 10. Computer 20 will be appreciated therefore to encompass any microprocessor, microcontroller or other processor and associated hardware and software.

Sample aliquots of fluid that are to be analyzed are acquired and controlled by the fluid control and handling components of manifold assembly 18, as described below, and are injected into a selected separation column. The chromatograph 10 shown schematically in FIG. 1 is a dual column chromatograph. The fluid control and handling components of manifold assembly 18 thus fluidly route the sample aliquots to a selected one of the separator columns labeled 26 and 28.

Analyte separation in separator columns 26 and 28 is carried on under controlled conditions as is well known in the art. For instance, the separation columns are contained within a temperature-controlled cabinet. Likewise, all components of chromatograph 10 are contained within appropriate housings, none of which are shown in the figures but which will be understood as being necessary to accurate analysis.

Analytes separated in the separation columns flow from the columns into a detector 30, which in the preferred embodiment is a thermal conductivity detector having dual thermistors. Since the preferred detector 30 is a dual thermistor unit there is a constant flow of carrier fluid 16 through the system. Carrier fluid 16 flowing through the non-analyzed state of the system exhausts to the atmosphere at exhaust port 32 on detector 30.

Analytical data compiled by detector 30 from the analyzed sample is transmitted to computer 20 where it is further processed according to software stored in the computer. Analytical results may then be transmitted from the computer through telephony equipment 24 on an automated basis, or the data may be acquired on prompt from a remote location. Analyzed fluid is exhausted through exhaust port 32.

As previously noted, chromatograph 10 is designed for remote automated operation, and is adapted for installation in harsh and extreme environments such as electric power transformers located in remote areas. The sample source in this situation would be the oil contained within an oil-blanketed transformer or other oil-filled electric power transmission device. Aliquots of fluid samples are obtained by extraction of the gas from the oil, or by drawing samples of the gas from a headspace in the device. Computer 20 is programmed to control all fluid flow through chromatograph 10.

Manifold Assembly

Figure 5:
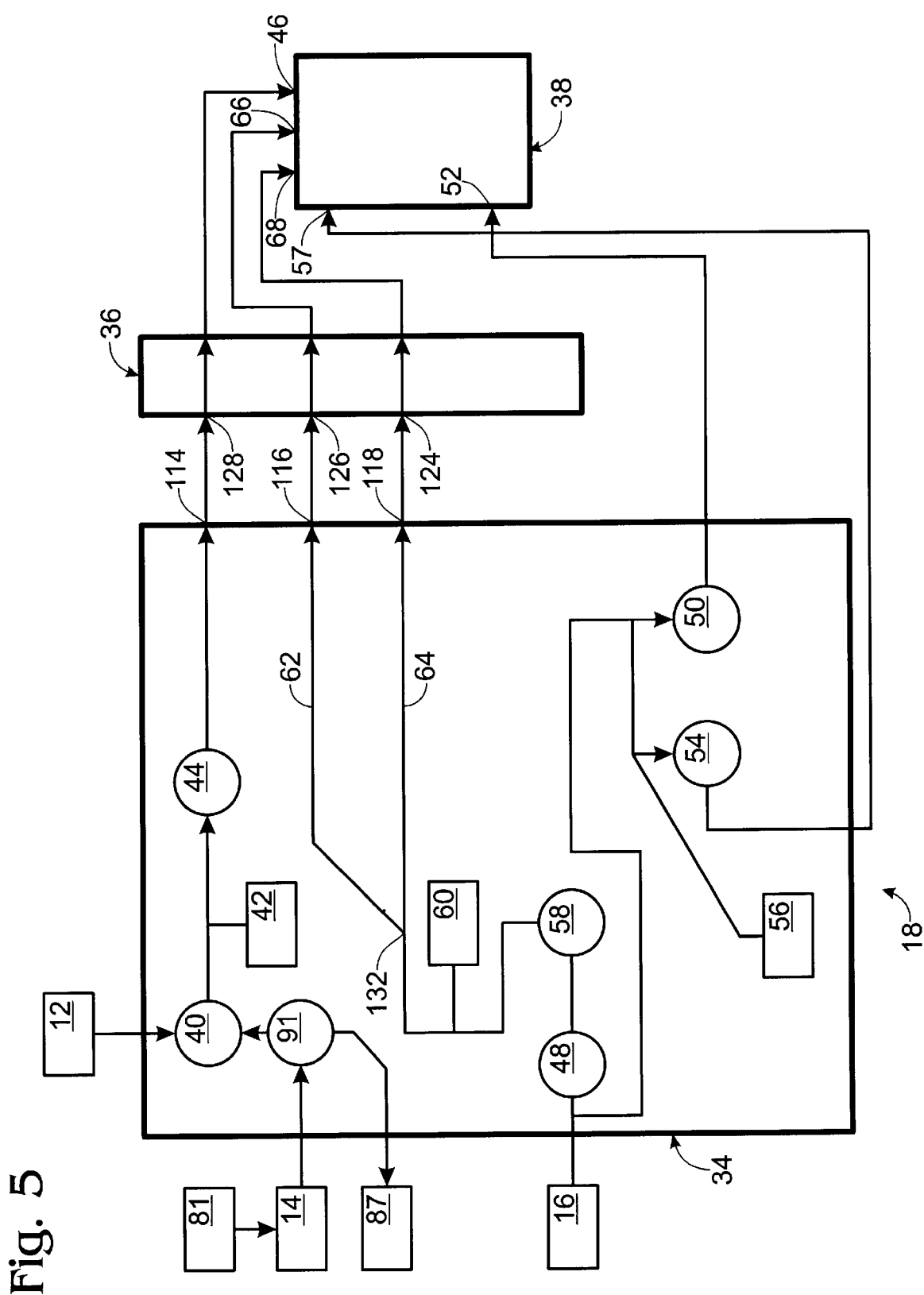
FIG. 5 is a simplified block diagram showing the fluid flow interconnections of the manifold assembly, collar assembly and injection valve of the present invention.

The fluid flow paths and connections in manifold assembly 18 are shown schematically in FIG. 5. Manifold assembly 18 includes as component parts thereof a manifold block 34, and a collar 36 that adapts block 34 to a rotary injector valve 38. Each of these components is described in detail below, and each of the active fluid control devices in manifold assembly 18 is under the control of computer 20. The fluid connections to and within manifold block 34 include calibration gas 12, which is fluidly connected to first control valve 40. First control valve is a three-port solenoid valve. A pressure transducer 42, operatively connected to computer 20 in the manner described below, is in the fluid path between control valve 40 and control valve 44, which also is a solenoid valve. Pressure transducer 42 is the pressure transducer associated with the sample aliquot control devices. Similarly, sample gas 14, which is the gas samples extracted in the extractor assembly 11, is delivered to control valve 91. Control valve 91 is also a three-port solenoid valve that is under the control of computer 20. Except when a sample analytical run is being made, control valve 91 is in a "normally closed" state such that sample gas 14 is being fluidly returned through the second port in the valve to tubing 85 and back to the extractor assembly. The third port of control valve 91 is connected to the third port of first control valve 40. As detailed below, when a sample analytical run is being made control valve 91 is switched so that the flow path of sample gas 14 is directed from valve 91 to valve 40. Thus, during an analytical run the fluid path of sample gas 14 is through control valve 91, then through first and second control valves 40 and 44, then through collar 36 to port 46 on rotary injector valve 38.

As detailed below, there are three pressure transducers associated with manifold block 34. Each transducer is associated with a specific flow path, and each is operatively connected to computer 20. Each transducer in the system provides pressure data value to the computer, and the computer is programmed to assign a value to the data received from the transducers.

Carrier fluid 16 is piped to manifold block 34 as described above with tubing and is directed in a fluid path within bock 34 to control valve 48. Control valve 48 is a pressure valve that controls flow of carrier fluid 16 in an on/off manner. Carrier fluid 16 is delivered to block 34 and to control valve 48 in a relatively higher pressure than the pressure of the gas downstream of control device 58, as described below. Relatively higher pressure carrier fluid is also delivered in the carrier fluid flow path within block 34 to a control valve 50. Control valve 50 is a two-position actuator valve, which, as detailed below, fluidly directs carrier fluid 16 to rotary injector valve 38 at port 52 to drive the injector valve between two operative states. A control valve 54, which also is a two-position actuator valve, is connected in the fluid path for carrier fluid 16. A pressure transducer 56 is in the fluid path associated with carrier fluid delivery to control valves 50 and 54, and more specifically, with the control of carrier fluid as an actuator of the rotary injection valve 38. Carrier fluid 16 is directed in a flow path from control valve 54 out of block 34 to rotary injector valve 38 at a port 57.

Pressure transducer 56 is used to measure the operating pressure of carrier fluid in the flow path to valves 50 and 54. And as noted above, gas pressure-related data transmitted from the transducer is analyzed by computer 20 to assign a value to the pressure. During operation of chromatograph 10, computer 20 determines if there is sufficient pressure of carrier fluid 16 in the flow path through valves 50 and 54 to adequately operate valve 38. Stated otherwise, computer 20 determines if the value assigned to the data received from transducer 56 is above a preprogrammed threshold value. This is done by comparing the assigned value with the programmed value. If the assigned value is below the threshold programmed value then computer will not allow the system to operate.

Returning to control valve 48, carrier fluid 16 is fluidly directed in a path to a further control valve 58, which is a manually operable pressure regulator valve, when control valve 48 is in the open state. Control valve 58 provides for adjustment of the pressure of carrier fluid 16 and may be set manually in the laboratory before installation of the unit, or in the field during operation and maintenance. In operation, the operating pressure of carrier fluid 16 is reduced at control valve 58 such that carrier fluid downstream of valve 58 is at a relatively lower pressure than the carrier fluid upstream of valve 58. Valve 58 thus serves to step down the operating pressure of carrier fluid 16. Fluid flow out of control valve 58 is past a pressure transducer 60 and out of block 34 in two separate flow paths, which diverge from one another at node or junction 132. Thus, carrier fluid 16, which is the system control gas, flows out of control valve 58 in two separate paths in block 34. The first system gas flow path is labeled 62 and exits block 34, flows through a fluid path through collar 36 and to port 66 on valve 38. Second system gas flow path 64 exits block 34, flows through collar 36 and to port 68 on valve 38. Pressure transducer 60 is associated with the lower pressure system gas.

Figure 6:
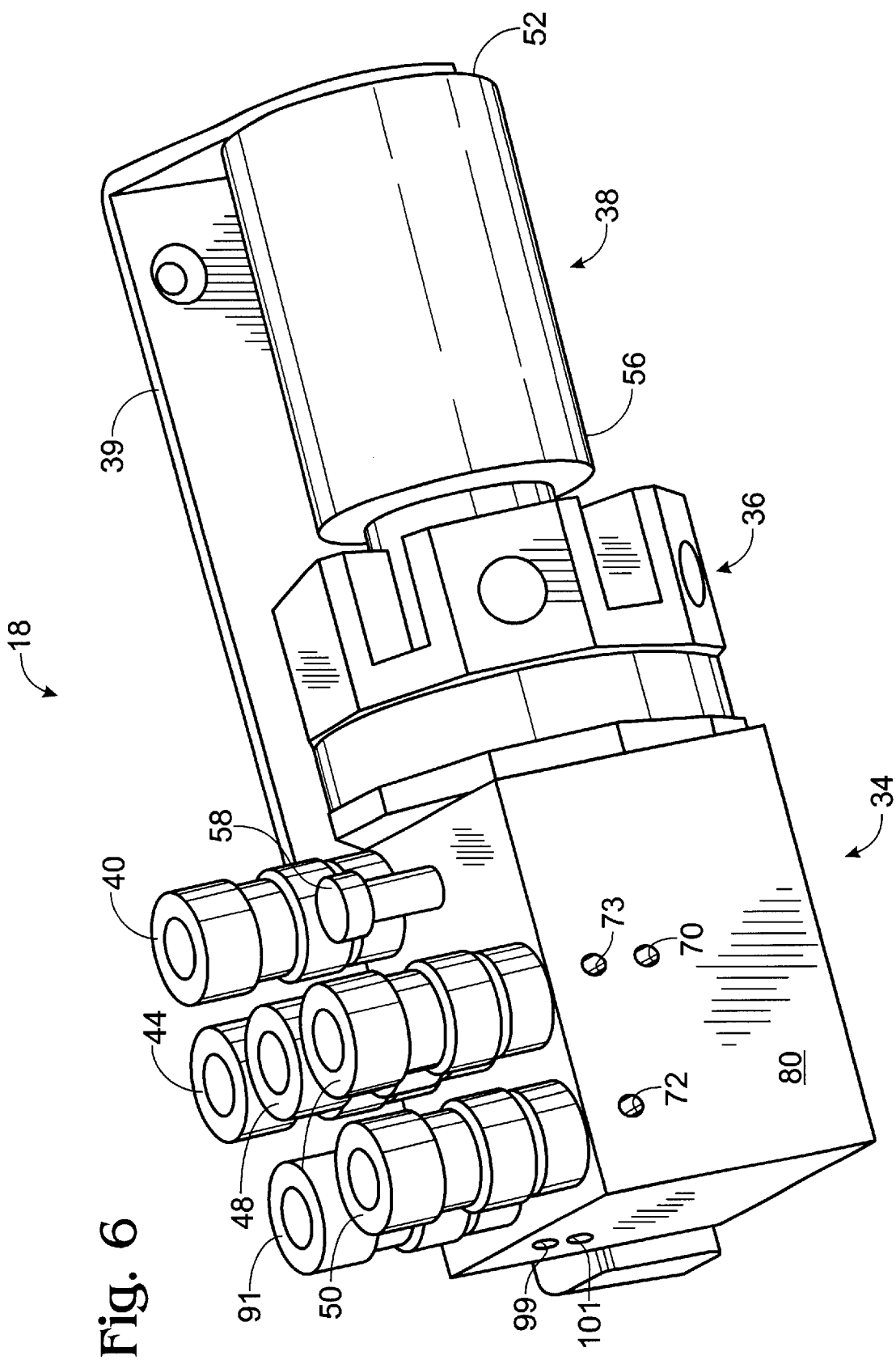
FIG. 6 is a perspective view showing the manifold assembly and some of its component parts.

Referring now to FIG. 6, manifold assembly 18 is shown with its component parts, namely manifold block 34, collar 36 and rotary injector valve 38. A mounting bracket 39 is also shown in FIG. 6. The function of bracket 39 is to mount manifold assembly 18 in a housing in chromatograph 10. None of the fluid connections external to manifold assembly are shown in FIG. 6. Carrier fluid 16 enters block 34 at inlet port 70. As noted above, carrier fluid 16 is delivered to block 34 from its external source (such as a pressurized gas cylinder) through appropriate tubing, and the tubing is connected to block 34 with appropriate fluid-tight fittings. Carrier fluid flows to port 52 on injector valve 38 through control valve 50, exiting block 34 at outlet port 72. Although not shown, port 72 is fluidly connected through tubing to port 52. Carrier fluid 16 also is delivered through control valve 54 out of block 34 by way of outlet port 73 to port 56 on injector valve 38. Similarly, sample gas is delivered to manifold block 34 through port 99 and thus to control valve 91. In the normally closed state, sample gas is returned to extractor assembly 11 through port 101. Both ports are connected as noted above with appropriate fluid-tight fittings to tubing 85 (FIG. 5).

Figure 7:
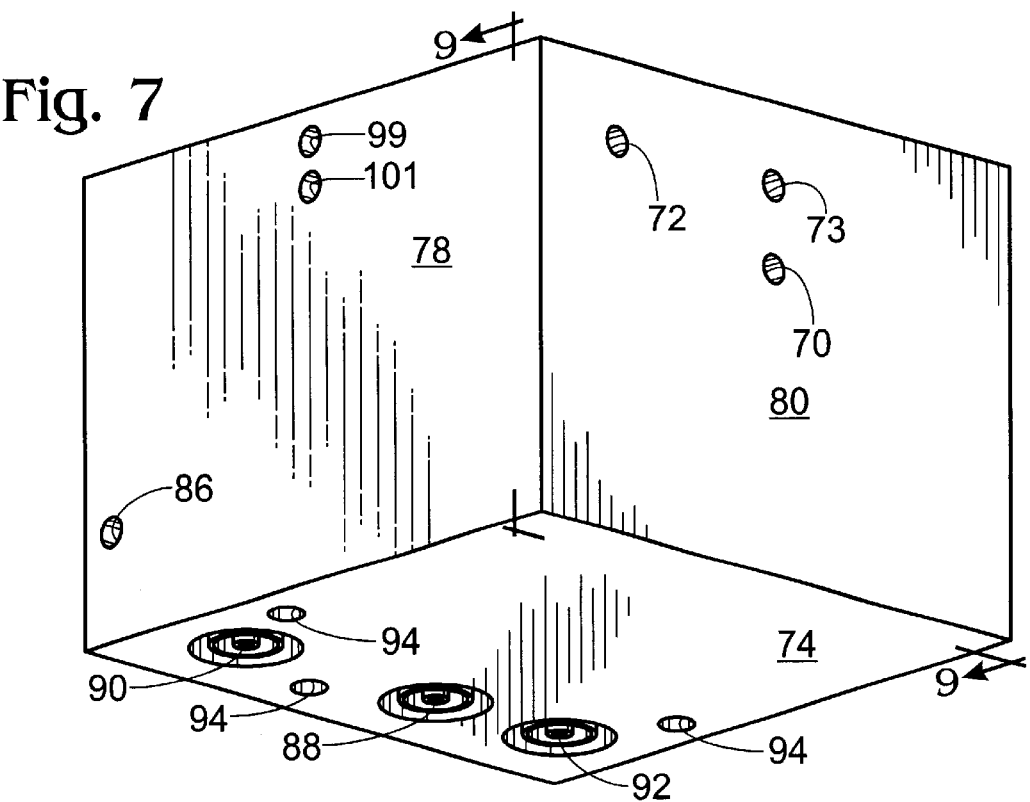
FIG. 7 is a bottom perspective view of the manifold block.

Manifold block 34 is shown in isolation in FIG. 7 and may be seen as a generally rectangular block having six faces. The three faces shown in FIG. 7 are labeled bottom face 74, first side face 78 and second side face 80, which is immediately adjacent face 78. The remaining three faces of block 34 are shown in FIG. 8, and include top face 76, third side face 82, and fourth side face 84.

Returning to FIG. 7, a bracket screw hole 86 is provided in first side face 78 for receiving a screw inserted through mounting bracket 39. Carrier fluid 16 inlet port 70, and carrier fluid outlet ports 72 and 73, which supply actuating fluid to injector valve 38, may be seen on the immediately adjacent second side face 80. Sample gas inlet port 99 and sample gas outlet port 101, both of which are fluidly connected to control valve 91, are formed in face 78.

The three pressure transducers 42, 56 and 60 are mounted on block 34 with fluid-tight connections on bottom face 74. Thus, there is a pressure transducer mounting receptacle 88 for receiving pressure transducer 42, a mounting receptacle 90 for receiving pressure transducer 56, and a mounting receptacle 92 for receiving pressure transducer 60. Each receptacle accommodates a double O-ring, and as may be seen, each receptacle includes an inner and an outer coaxial O-ring seat. Each of the three pressure transducers are held in their respective receptacles against the double O-rings in a fluid-tight seal with a pressure transducer plate (not shown), which mounts to bottom face 74 with three screws through the plate and fitting into screw holes 94. The plate is tightened with screws, thereby exerting pressure on the pressure transducers and providing a fluid seal. The pressure transducers are operatively connected to computer 20 through a circuit board mounted on fourth side face 84, as described below.

Figure 8:
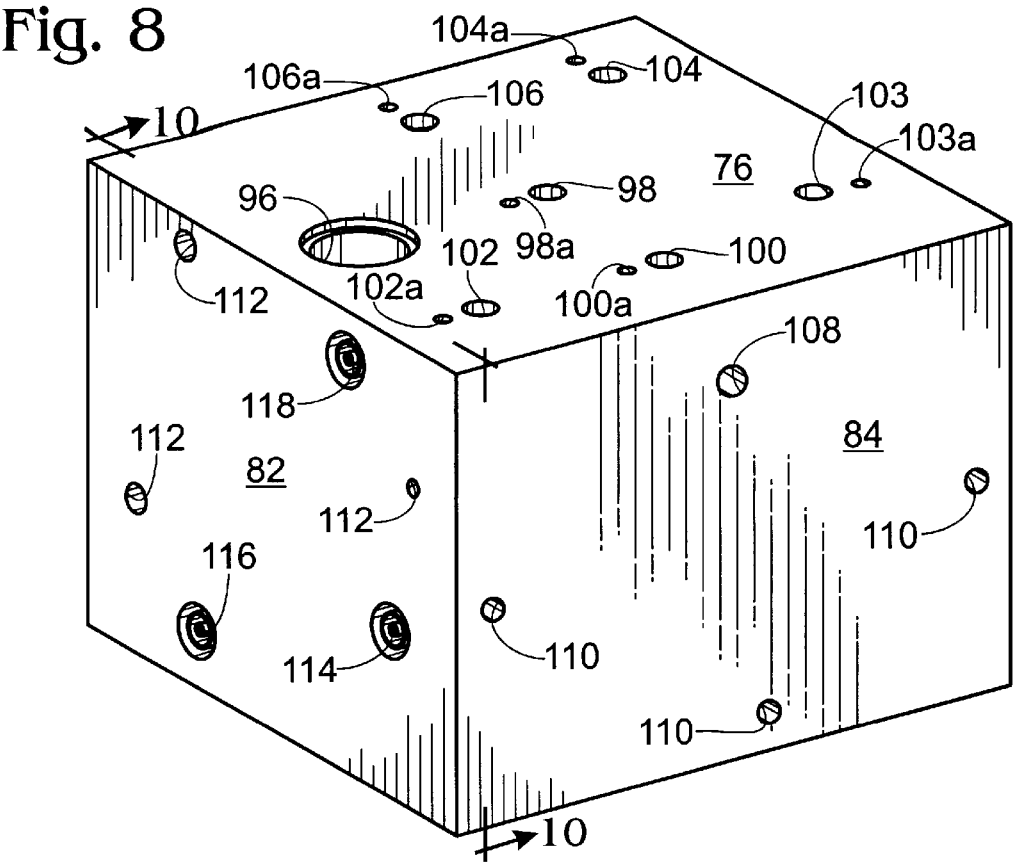
FIG. 8 is a top perspective view of the manifold block.

Referring to FIG. 8, the fluid control device mounting locations may be seen on top face 76 and third and fourth side faces, 82 and 84, respectively. Control valve 58—the manually operable pressure regulator—is mounted in port 96. Control valve 48 is mounted in port 98. Control valve 91 is mounted in port 103. Control valve 40 (the first solenoid valve) is mounted in port 102, and control valve 44 (the second solenoid valve) is installed in port 100. Control valves, 50 and 54, which are the two actuator valves, are mounted in ports 104 and 106, respectively.

Each of the control valves installed on block 34 is a three-port valve, although in all instances except control valves 40 and 91 only two ports are used. As such, for each control valve mounting port 98, 100, 102, 104 and 106 there is an associated port 98a, 100a, 102a and so on. These associated ports are fluidly interconnected with the mounting ports, as detailed below. With regard to control valve 40, sample source 14 is fluidly connected from control valve 91 to an inlet port on the valve itself, which as noted is a three-port valve in which each of the three ports is utilized.

An inlet port 108 is provided on fourth side face 84 for the connection with a supply of calibration gas 12. Three pressure board mounting holes 110 are drilled into face 84. A pressure board (not shown), which is a printed circuit board designed to supply an interface between the pressure transducers and the computer control system, is mounted to face 84 at the three mounting holes 110. Standoffs are positioned between the pressure board and the face of the block to physically separate the board from the block and to allow spacing for electrical connections. Specifically, each electrical lead on each of the pressure transducers is soldered to an associated pad on the pressure board. The pressure board is then electrically connected to computer 20 with appropriate cabling.

Collar 36 is mounted to third face 82 of block 34 with screws into three threaded collar mounting holes 112. There are three fluid connections that flow directly between face 82 of block 34 and collar 36, and for each there is an O-ring seal that provides a fluid-tight, leak-free seal. The first fluid registry leading from block 34 to collar 36 is at port 114, which is the fluid path that is connected to port 46 of injector valve 38. Stated otherwise, port 114 is in the fluid path for the sample fluid flowing through the manifold assembly. This is the sample that will be separated and analyzed in the separator columns 26 and 28. As may be seen, there is a seat surrounding the port on block 34 for receiving an O-ring. The second and third fluid registries between block 34 and collar 36 are for carrier fluid 16, which as noted earlier are delivered to ports 66 and 68 of valve 38. There are thus ports 116 and 118 on face 82, each of which provides the fluid path for carrier fluid 16 from block 34 to collar 36. Again, there are seats surrounding the ports on the face of block 34 for receiving O-rings to provide a fluid-tight seal.

Figure 9:
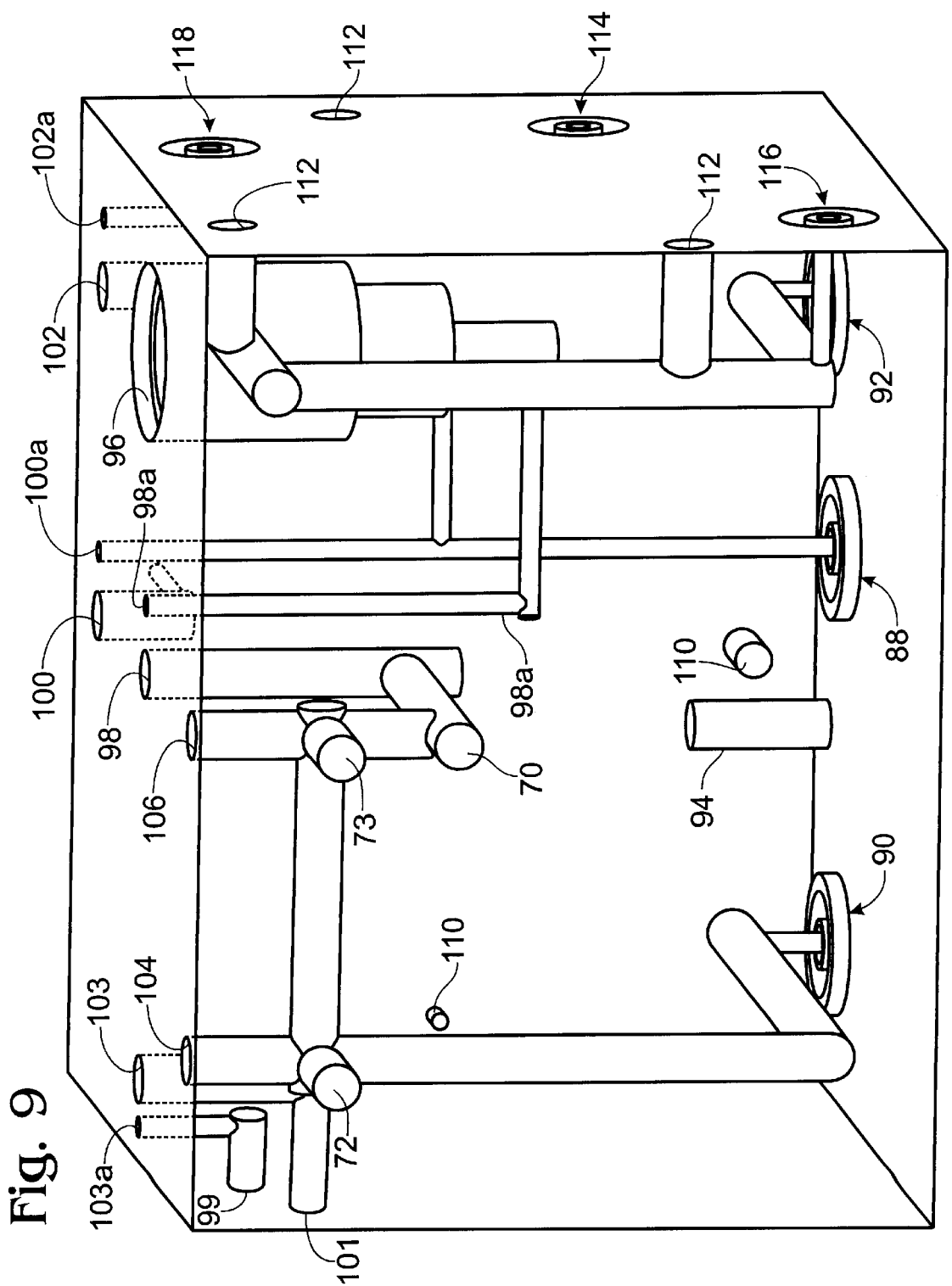
FIG. 9 is a perspective cross sectional view of the manifold block taken along the line 9—9 of FIG. 7, showing the fluid flow paths through the manifold in reverse shading.

A perspective cross sectional view of the fluid connections and paths in manifold block 34 is shown in FIG. 9. The view of FIG. 9 will be understood to show the fluid paths through manifold block 34 in reverse text—that is, the solid portions of the block are shown to be hollow and the hollow portions (i.e., the fluid paths) are shown to be solid. In addition, it will be appreciate by those skilled in the art that to make the fluid paths shown in the figures it is necessary to drill various holes into the block that must later be plugged in a fluid-tight manner. In this regard, block 34 is fabricated from an appropriate material to be resistant to degradation from the kinds of fluids that flow through it. Typical materials for block 34 are anodized aluminum alloys and stainless steel. In fabricating block 34 the necessary holes are drilled to provide the desired fluid connections, for instance with milling machines under computer numeric control, and then the access holes that were necessary to drill the desired fluid connections but which are not needed after drilling are plugged.

Figure 10:
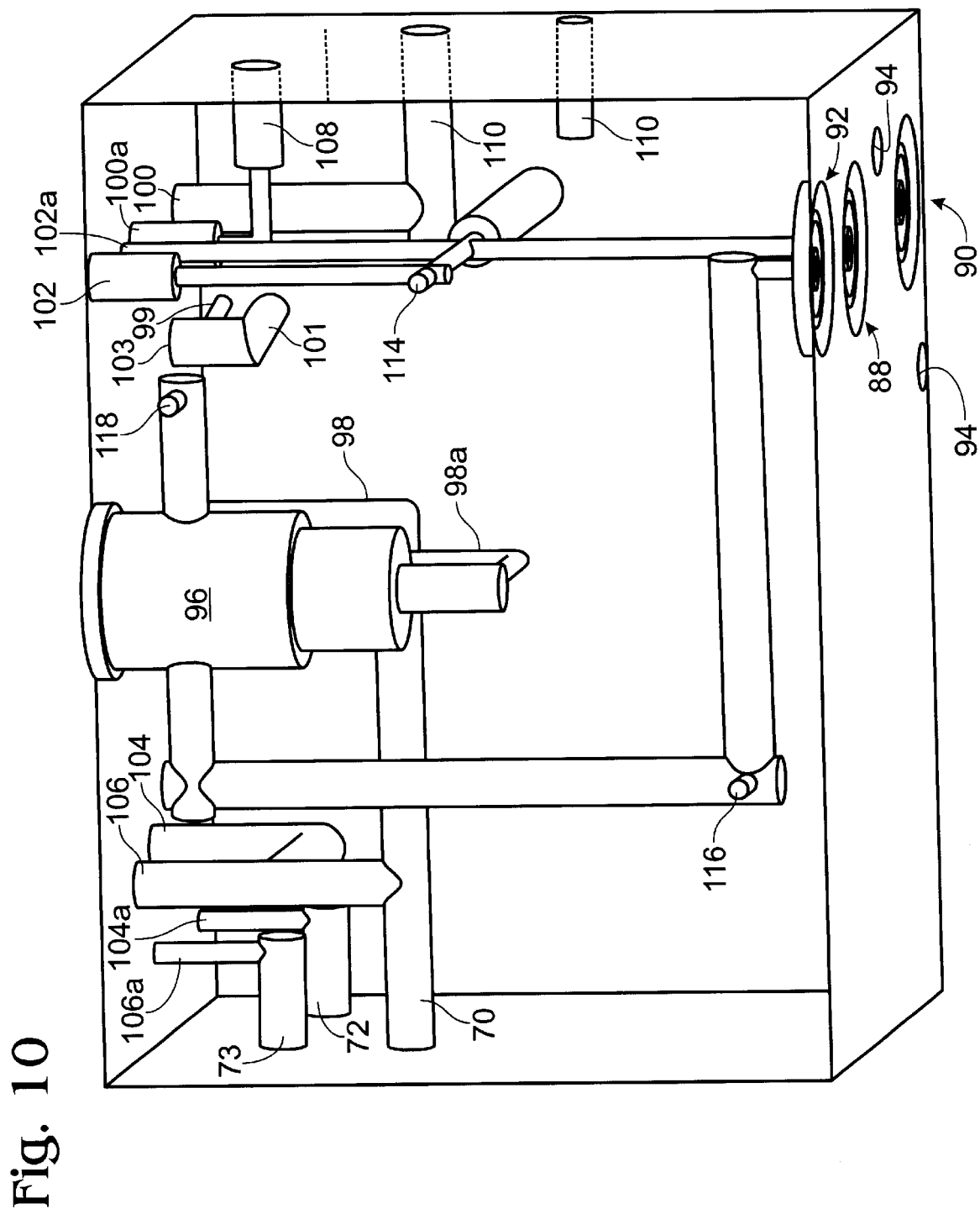
FIG. 10 is a perspective cross sectional view taken along the line 10—10 of FIG. 8, showing the fluid flow paths through the manifold in reverse shading.

A perspective cross sectional view of the fluid connections and paths in manifold block 34, taken through another face of the block compared to FIG. 6, is shown in FIG. 10. The fluid flow channels illustrated in FIGS. 9 and 10 may be traced in combination with the fluid path schematic diagram of FIG. 5 to follow each separate fluid path through the manifold block.

Figure 11:
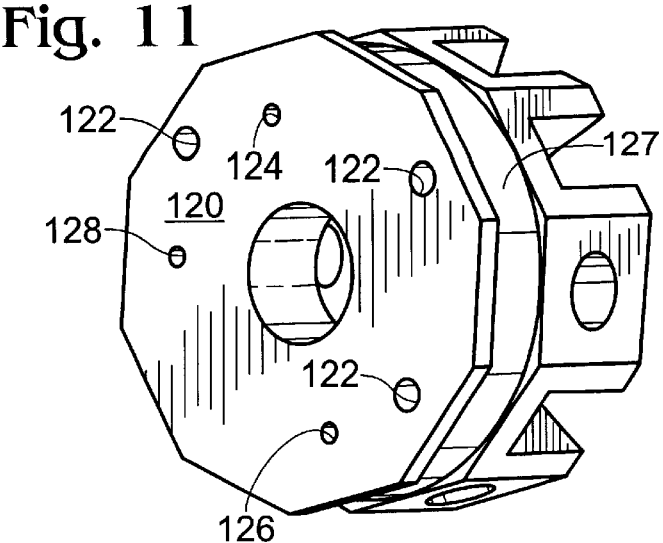
FIG. 11 is a perspective view of the adapter collar showing the face of the collar that joins the manifold block when the two are assembled.

The collar 36 is mounted to third face 84 of block 34, as noted earlier. FIG. 11 shows the mounting face 120 of collar 36 and includes three mounting holes 122 that align with threaded mounting holes 112 in face 84. When collar 36 is mounted to block 34, port 124 in collar 36 aligns or registers with port 118 in block 34 to define a fluid path from the block into the collar, and is fluidly sealed against the O-ring that is associated with port 118. Likewise, port 128 aligns with and seals against port 114, and port 126 aligns with and seals against port 116, again defining fluid paths from the block into the collar. As may be seen in FIG. 11, collar 36 includes a groove 127 that encircles the collar. Although not shown in the drawings, the two sample loops 142 and 148, which are relatively long, thin tubing, are typically wound around the collar in groove 127. The opposite ends of the sample loops are connected to separate ports of the injector valve 38 as described below.

Figure 12:
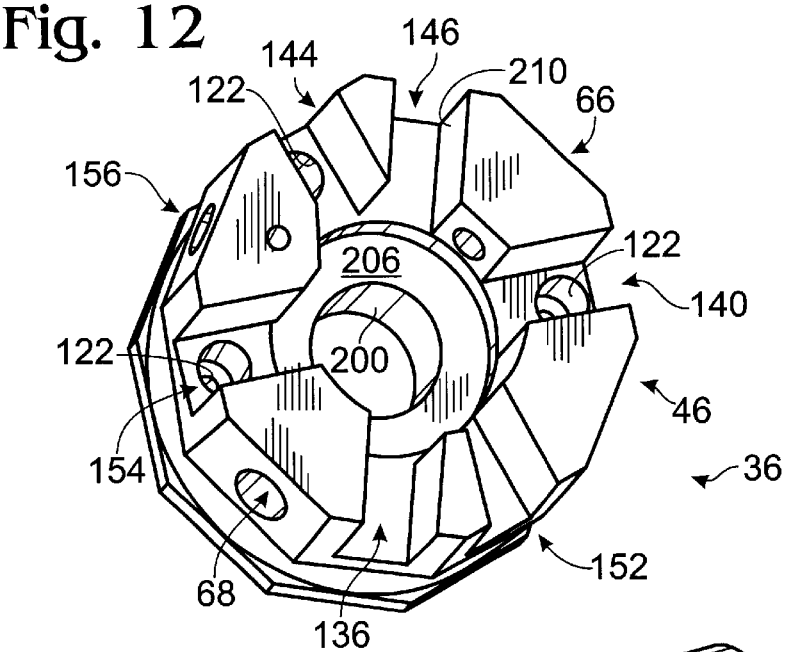
FIG. 12 is a perspective view of the opposite side of the adapter collar.

The opposite face of collar 36 that mates to injector valve 38 is shown in FIG. 12. Like block 34, collar 36 includes plural internal fluid pathways that provide fluid connections between block 34 and valve 38, and which are drilled with CNC controlled milling equipment. Collar 36 is preferably made of an anodized aluminum alloy or stainless steel.

Figure 13A:
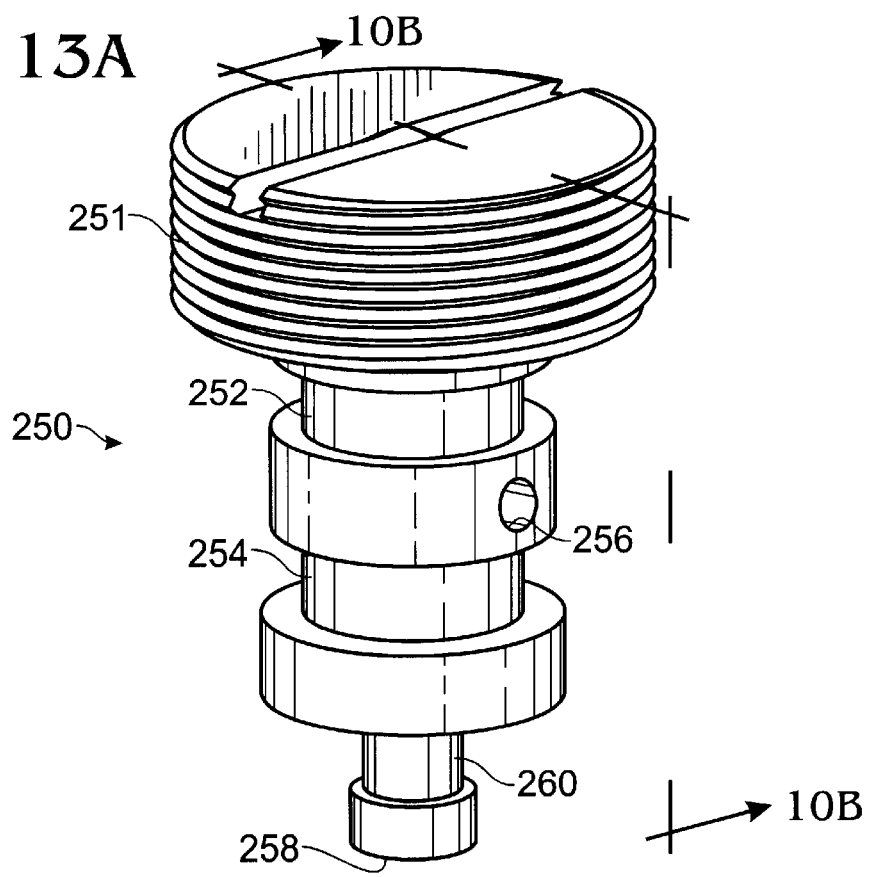
FIG. 13A is a perspective view of a port fitting that is used in conjunction with the adapter collar.
Figure 13B:
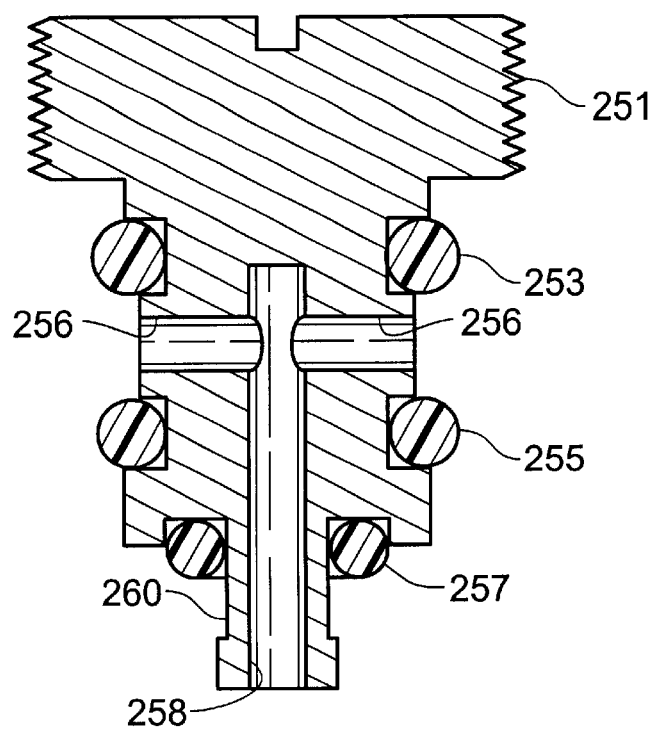
FIG. 13B is a cross sectional view through the port fitting shown in FIG. 13A, taken along the line 13B—13B of FIG. 13A.

A port fitting 250 that is used in connection with collar 36 is shown in FIGS. 13a and 13b. With reference to FIG. 13a, port fitting 250 is shown as having a threaded head region 251 that engages cooperatively threaded portions in ports labeled 46, 66, 68 and 156 in collar 36 (FIG. 12)(the threaded portions are not illustrated). Port fitting 250 includes two spaced apart seats 252 and 254 for receiving O-rings 253 and 255 (FIG. 13b), respectively that provide a seal between the port fitting and the interior walls of the ports in collar 36. A fluid channel 256 is provide entirely through fitting 250 between seats 252 and 254. Channel 256 intersects within fitting 250 with a transverse fluid channel 258 that exits the distal end of port fitting 250 through barrel 260.

Each of the ports 46, 66, 68 and 156 in collar 36 includes fluid channels into the interior walls of the ports. With fitting 250 inserted into these ports, the fluid channels into the ports register with the fluid channel 256 of the fitting, thereby providing a fluid path through barrel 260. The O-rings 253 and 255, which are on either side of the registry with channel 256, provide for a fluid-tight seal.

Figure 14:
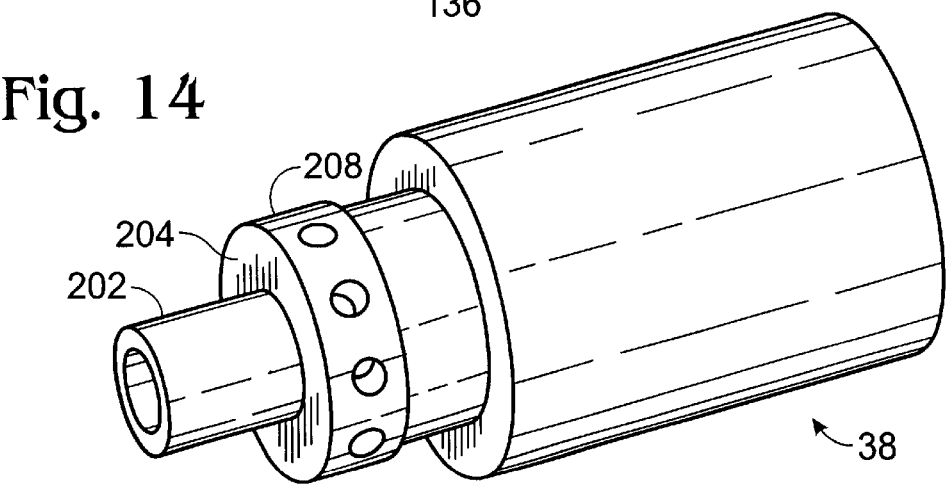
FIG. 14 is a perspective schematic view of a rotary injection valve used in the present invention.

As shown in FIG. 6, and as explained herein, valve 38 is mounted to collar 36. In the preferred embodiment injector valve 38 is a two position, ten port, fluid actuated, conical rotary injection valve. Valves of this kind are available from Valco Instruments Co., Inc. A schematic representation of injector valve 38 is shown in FIG. 14. Each port utilizes a zero-dead-volume ferrule having pre-installed O-rings (not shown). Port fittings 250 are screwed into each of the ports 46, 66, 68 and 156 in collar 36 such that barrel 260 extends into a central aperture 200. When valve 38 is mated with collar 36 as shown in FIG. 3, a cylindrical extension 202 extends through aperture 200 and a shoulder 204 abuts a cooperatively formed cylindrical seat 206 on the collar.

Valve 38 includes ten ports that radiate from a hub 208. When valve 38 and collar 36 are connected the ports on valve 38 register with the interior distal ends of the port fittings 250 such that the port fittings make fluid connections through the collar to the valve. More specifically, the distal (interior) ends of port fittings 250 engage and are received into the aligned associated ports on valve 38. An O-ring 257 on port fitting 250 seats against an exterior portion of the ports on hub 208, and the distal end of each barrel 260 seats against the pre-installed O-ring in the ports to provide a fluid-tight connection. In this way valve 38 is connected to collar 36 by virtue of these fluid connections, and valve 38 is suspended in aperture 200.

The relative locations of the ports on injector valve 38 in relation to the associated fitting locations on collar 36 are shown in FIG. 12.

Thus, referring to FIG. 12, port 146 of valve 38 aligns with a radial slot 210 formed in collar 36. Port 146 includes a fluid connection through appropriate tubing to separator column 28 (not shown in FIG. 12). Fluid flowing out of port 146 thus flows through the separator column, and to the downstream thermal conductivity detector 30. The adjacent port 66 of valve 38 is fluidly connected to port 124 of block 34 and provides one fluid path for carrier fluid 16 through a port fitting 250 in the manner described above. Fluid flow from the next adjacent port 140 on valve 38 is to sample loop 142, the function of which is described below, and continuing on to port 144 of the valve. Sample loop 142 is a standard sample loop that is not shown in FIG. 12. Port 156 is fluidly connected to exhaust port 130 through exhaust port connection 212 and port fitting 250 that resides in port 156. Continuing around the ports on valve 38 from port 140, the next adjacent port 46 is fluidly connected to port 128 through the port fitting 250 in port 46, which is in the fluid path delivering samples from sample source 14. Port 152 of valve 38 is plumbed to sample loop 148 and returns to valve 38 at port 154. Port 136 directs fluid flow to separator column 26. Finally, port 68 is fluidly connected through collar 36 to port 116 of block 34, which provides one of the fluid paths for carrier fluid 16 through a port fitting 250 in port 68. As noted above, while not shown, both of the sample loops are wound around collar 36 in groove 127 (FIG. 11).

Two State Operations

Figure 15:
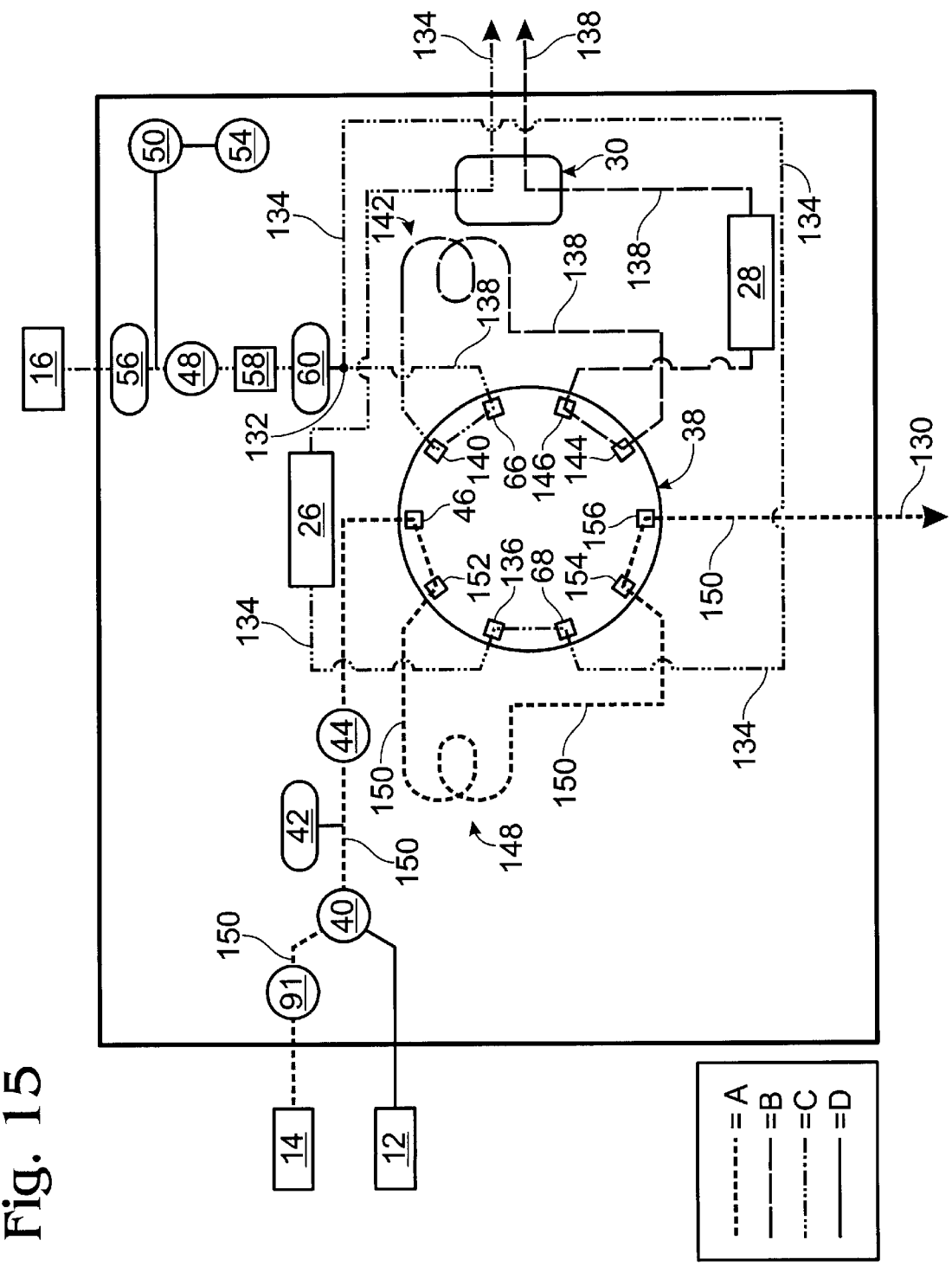
FIG. 15 is a semi-schematic block diagram and flow chart showing fluid flow through the analytical instrument including the components of the present invention, in which the valve system is in a first state condition.

Having described the fluid flow paths through manifold assembly 18 and its component parts, the two alternate states of the injector valve 38 and the associated fluid flow paths will now be described. With reference to FIG. 15 a schematic representation of the fluid flow paths through gas chromatograph 10 when injection valve 38 is in a first position, or an "A" state is shown. As noted above, valve 38 is a ten port rotary injection valve having two positions, or states. In the preferred embodiment, valve 38 is pneumatically actuated, and hence is driven selectively between the two state positions by fluid pressure through control valves 50 and 54, which are in turn under the control of computer 20. Carrier fluid 16 provides the fluid pressure for operating control valves 50 and 54, that as noted are actuator valves.

System Equilibration and Sample Aliquot Acquisition

As noted earlier, contaminants of interest contained in oil filled device 3 are allowed to diffuse from the first liquid phase into the second liquid phase in extractor assembly 11. In this regard, during a sample equilibrium and acquisition phase oil is continuously circulated through the extractor assembly, returning as described earlier to the oil filled device. As the oil flows through the extractor assembly, and thus past filter 29 and its plural separator tubes, dissolved gas contained in the oil diffuses across the tubular filter media into the second phase. This second phase, which comprises gaseous fluid, is periodically circulated in set time intervals to assure that all fluid in the second phase is homogeneous and until equilibrium conditions are reached. Stated otherwise, principles of diffusion dictate that the contaminants in the oil diffuse across the filter media from an area of relatively higher concentration to an area of relatively lower concentration until equilibrium (or conditions near to equilibrium) is reached.

Equilibrium and the rate of diffusion across the filter media are influenced by many different factors. In practice, it has been found that with the filter cartridge 29 described above, equilibrium is achieved in around 2 hours at an oil flow rate of between about 150 to about 250 ml per minute. Since diffusion rates are also temperature dependent, the temperature of the oil is monitored at thermocouple 97.

When computer 20 determines that it is time to inject a sample of gas into chromatograph 10, or when computer 20 is prompted to do so externally, control valve 87 (FIG. 1) switches to a closed position and gas pump 81 is switched on to compress the gas contained in the extractor system into the gas sample line. This creates a pressure differential across the valve. It also essentially creates a closed loop containing the desired sample aliquot in the gas space existing from gas pump 81, through control valve 91 and back to control valve 87. At this point computer 20 determines the pressure of gas at transducer 83. If the pressure exceeds a predetermined minimum threshold value, then the computer determines that there is sufficient pressure to analyze the aliquot and continues with the analytical processing.

Simultaneously with the equilibration and sample acquisition step, and prior to operation of chromatograph 10 the system begins in the A state to allow equilibration of the chromatograph system with pure carrier fluid 16, which as noted is typically an inert gas such as helium. This allows any fluid in the separation columns 26 and 28 to elute and be flushed through detector 30 and to be vented to atmosphere at 134 and 138. With reference to FIG. 15, the chromatographic equilibration step is carried out with control valve 44 closed. Control valve 40 is at all times selecting for one or the other of sample fluid 14 or calibration fluid 12, and pressure transducer 42 is, in combination with computer 20 as described above with reference to transducer 56, determining if there is sufficient operating pressure in the flow path to valve 44 for sufficient operations. Simultaneously, computer 20 is determining if there is sufficient pressure in the carrier fluid flow path through valves 50 and 54 to ensure proper operations. This is done by comparing the data from transducer with assigned values stored in the computer 20, as described above.

The chromatographic equilibrium flushing of carrier fluid is allowed to continue for a set time period of a known duration, which correlates to the time necessary to completely elute any sample fluid from the separator columns.

Fluid Flow in State A and B Operations

Once chromatograph system equilibrium is achieved, control valves 91 and valve 40 are switched under the control of computer 20 to select for sample fluid 14 (line A in FIG. 15), and valve 44 is allowed to open with pressure transducer 42. With valve 38 in the first state position shown in FIG. 15, a sample aliquot from sample source 14 is metered into sample loop 148, charging that sample loop with sample fluid. This is shown with line A in FIG. 15, labeled with reference number 150. The sample is allowed to flow into sample loop 148 for a predetermined time period sufficient for the sample loop to be fully charged.

Figure 16:
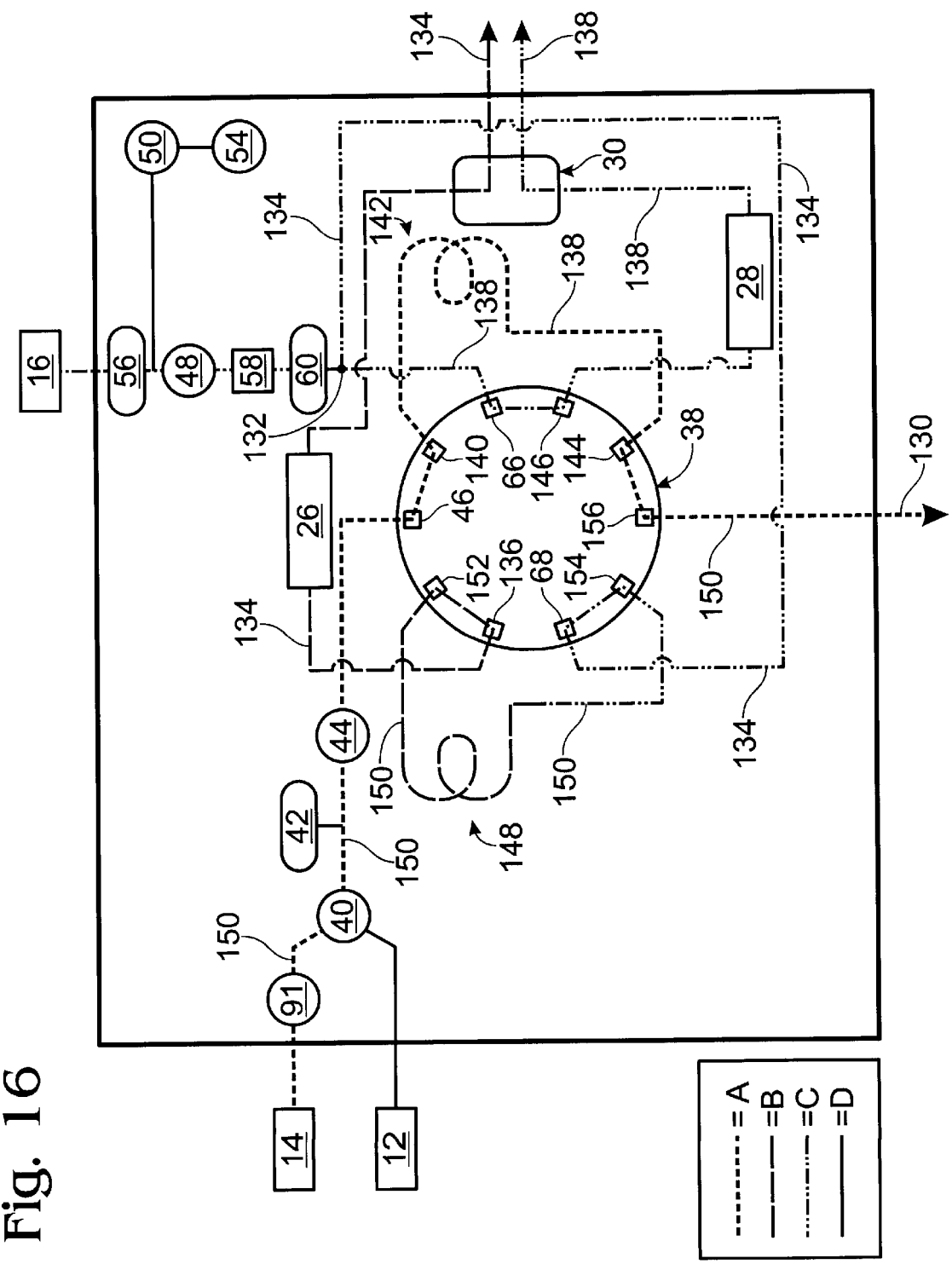
FIG. 16 is a semi-schematic block diagram and flow chart showing fluid flow through an analytical instrument including the components of the present invention, in which the valve system is in a second state condition.

Once sample loop 148 is fully charged, valve 44 closes and valve 38 is immediately switched to the state B mode shown in FIG. 16. When in state B, the sample fluid in sample loop 148 is injected into column 126 by carrier fluid 16 directed through the flow path 134 shown by line C in FIG. 16. Thus, the sample fluid being analyzed is shown as line B, and the carrier fluid that is pushing the sample fluid through the loop is shown as line C. Sample fluid is driven through column 26 by the pushing pressure of carrier fluid. Analytes are separated in column 26, eluted out of the column and through detector 30, ultimately venting to atmosphere at 134.

In the schematic illustrations of FIG. 16 the sample fluid aliquot is arbitrarily shown as beginning somewhere upstream of the beginning of sample loop 148. It will be appreciated that this is for illustrative purposes only, and that in actuality the partition between the sample aliquot and the carrier fluid that pushes the aliquot through the separator column and the detector is a moving partition.

Once all analytes have been eluted from column 26 with valve 38 in state B (FIG. 16), valve 44 once again opens to charge sample into sample loop 142 (line A in FIG. 16, reference number 138), assuming extraction equilibration has been achieved at extractor assembly 11. It should be noted that correct analysis requires that a new sample be analyzed no more often than equilibration is achieved. Once a sample is thus correctly acquired, the loop is charged with fresh sample, valve 44 closes and valve 38 is immediately switched back to the state A mode (FIG. 15) and the sample contained in loop 142 is injected through valve 38 and through column 28 for separation and detection at detector 30 (lines B and C, reference number 138). Sample is vented to atmosphere from detector 30 at 138.

It will be appreciated that control valve 40 may also be directed under the control of computer 20 to select for a fluid flow of calibration gas 12 through the system, with the same two states of valve 38 as described above (i.e., line D in FIGS. 15 and 16). Calibration gas is used for standard purposes of verifying the calibration and accuracy of the both separation columns 26 and 28, and the proper functioning of detector 30. Thus, calibration gas 12 typically has known concentrations of selected analytes. When valve 40 is prompted to select calibration gas 12, the calibration gas flows through the selected one of the separation columns in the same two-state manner as described above. The analytical data can then be accessed to monitor the system and to recalibrate the system (remotely) if necessary.

The system of the present invention includes numerous safety features that are monitored by and under the control of computer 20, and which ensure accurate operation and maintenance of the system. Notable among these is the combined optical sensors 73 and 75. As described above, when sensor 73 detects fluid, valve 7 is switched so that the fluid that has seeped into the "gas" phase can be eliminated from that phase. The system includes a counter to determine how many times sensor 73 has detected such fluid and has switched the state of valve 7 to correct for it. Computer 20 includes a counter that monitors the number of such "events" as a measure of the effective life of filter 113. Once a maximum number of events have been reached, a maintenance reminder is transmitted from the computer. Finally, valve 77 in normal operations when the valve is powered is in a first position that allows gas to enter the second phase system. If power to the system is interrupted or lost, or if optical sensor 75 detects fluid, valves 77 switches to a power-off position to close the fluid pathway from the valve into the second phase side. Similarly, valve 87 switches to a power-off position to close the fluid pathway through that valve (see FIG. 1), effectively isolating any contaminants in the first phase side of the system. This prevents first phase fluid from entering the second phase side of the system in the event of system failure.

In view of the many possible embodiments to which the principles of our invention may be applied, it should be recognized that the detailed embodiments are illustrative only and should not be taken as limiting the scope of my invention. Rather, we claim as our invention all such embodiments as may come within the scope and spirit of the following claims and equivalents thereto.

What is claimed is:

1. Apparatus for extracting gas from fluid contained in a tank, and for analyzing the extracted gas, comprising:
   a fluid pathway for routing a fluid from said tank;
   a separator in the fluid pathway having an inlet for routing said fluid through said separator, and media for separating gas from said fluid to define a fluid phase and a separate gas phase, said separator defining a fluid phase flow path and an isolated gas phase flow path;
   a first outlet in said separator for routing said fluid through a fluid pathway to said tank, and a second outlet in said separator for routing said gas phase to a gas phase equilibration loop;
   a pump for circulating said fluid from said tank through said separator during an equilibrium state operation;
   a pump for circulating said gas phase in said gas phase equilibrium loop during said equilibrium state operation;
   at least one control valve in said gas phase equilibration loop for selectively routing said gas phase from said gas phase equilibrium loop to an instrument for analyzing selected components in said gas during a gas analysis state operation.

2. The apparatus of claim 1 including a plenum in the gas phase equilibrium loop for accumulating fluid contained in the gas phase.

3. The apparatus of claim 2 including means for detecting fluid in said plenum and control means for selectively routing said fluid in said plenum to said inlet on said separator.

4. The apparatus of claim 2 wherein said detecting means comprises optical detector means for detecting fluid in said plenum.

5. The apparatus of claim 1 including a manifold fluidly connected to said gas phase equilibrium loop for defining fluid flow paths for said gas and for a carrier gas to a gas separator column, the manifold assembly comprising:
   (a) a manifold block having a plurality of outer faces, a first fluid flow path for said carrier gas and a second fluid flow path for said gas, said first and second fluid flow paths including an inlet port and an outlet port, and at least one fluid control device in each of said first and second fluid flow paths for selectively controlling the flow of said carrier and sample gases, said control devices operatively under the control of a computer;
   (b) a collar mated to a face of said manifold block and having a first collar fluid flow path for said carrier gas and a second collar fluid flow path for said gas, said first collar flow path including an inlet port on the collar in registry with said outlet port in said first fluid flow path, and said second collar fluid flow path including an inlet port on the collar in registry with said outlet port in said gas flow path;
   (c) an injection valve attached to said collar and having ports fluidly connected to said first and second collar fluid flow paths, said injection valve configured for directing said carrier fluid and said gas to said separation column.

\* \* \* \* \*